United States Patent
Ball et al.

(10) Patent No.: US 10,775,381 B2
(45) Date of Patent: Sep. 15, 2020

(54) BIOMARKER SPAG5

(71) Applicants: Nottingham Trent University, Nottingham (GB); Nottingham University Hospitals NHS Trust, Nottingham (GB)

(72) Inventors: Graham Roy Ball, Nottingham (GB); Stephen Yan Tat Chan, Nottingham (GB); Tarek Mohamed Ahmed Abdel-Fatah, Nottingham (GB)

(73) Assignees: NOTTINGHAM TRENT UNIVERSITY, Nottingham (GB); NOTTINGHAM UNIVERSITY HOSPITALS NHS TRUST, Nottingham (GB)

( * ) Notice: Subject to any disclaimer, the term of this patent is extended or adjusted under 35 U.S.C. 154(b) by 264 days.

(21) Appl. No.: 15/417,511

(22) Filed: Jan. 27, 2017

(65) Prior Publication Data

US 2017/0138947 A1    May 18, 2017

Related U.S. Application Data

(63) Continuation of application No. 14/404,163, filed as application No. PCT/GB2013/051465 on May 31, 2013, now abandoned.

(30) Foreign Application Priority Data

Jun. 1, 2012 (GB) .................................. 1209802.6

(51) Int. Cl.
*G01N 33/574* (2006.01)
*C12Q 1/6886* (2018.01)
*C07K 16/18* (2006.01)
*G01N 33/577* (2006.01)
*C07K 16/30* (2006.01)

(52) U.S. Cl.
CPC ....... *G01N 33/57415* (2013.01); *C07K 16/18* (2013.01); *C07K 16/30* (2013.01); *C12Q 1/6886* (2013.01); *G01N 33/577* (2013.01); *G01N 33/5748* (2013.01); *G01N 33/57407* (2013.01); *G01N 33/57449* (2013.01); *C07K 2317/76* (2013.01); *C12Q 2600/106* (2013.01); *C12Q 2600/118* (2013.01); *C12Q 2600/158* (2013.01); *G01N 2800/52* (2013.01); *G01N 2800/7028* (2013.01)

(58) Field of Classification Search
None
See application file for complete search history.

(56) References Cited

U.S. PATENT DOCUMENTS

2011/0217297 A1    9/2011   Kao et al.

FOREIGN PATENT DOCUMENTS

WO    20100088386    8/2010

OTHER PUBLICATIONS

McCarty, Jr. et al. (Cancer Research (Suppl.) 46, 4244s-4248s, Aug. 1986).*
International Preliminary Report on Patentability for International Patent Application No. PCT/GB2013/051465 (dated Dec. 2, 2014).
Abdel-Fatah, Tarek "Study of Sperm-Associated Antigen 5(SPAG5) in Predicting Response to Anthracycline (ATC)/Platinum Chemotherapies (CT) in Breast (BC) & Ovarian Cancers (OVC)," The University of Nottingham Presentation Jun. 1-5, 2012.
Kwan et al. Cancer Res Apr. 15, 2010 70;3303 Abstract 3303: Investigation of SPAG5 gene expression as a molecular marker for breast cancer prognosis. Proceedings: AACR 101st Annual Meeting 2010—Apr. 17-21, 2010.
Kenneth S. McCarty, Jr. et al. Use of a Monocional Anti-Estrogen Receptor Antibody in the Immunohistochemical Evaluation of Human Tumors. Cancer Research (Suppl.) 46, 4244S-4248S, Aug. 1986.
International Search Report for PCT/GB2013/051465 dated Jul. 29, 2013.
Välk K. et al. Gene Expression Profiles of Non-Small Cell Lung Cancer: Survival Prediction and New Biomarkers. 79:283-292, published online Mar. 16, 2011.
Abdel-Fatah et al., "A Study of Sperm Associated Antigen 5 (SPAG5) in Predicting Response to Anthracycline (ATC)/Platinum Chemotherapies (CT) in Breast (BC) and Ovarian Cancers (OVC)" Journal of Clinical Oncology, 2012 ASCO Annual Meeting Proceedings, May 20, 2012, 230 (15): 1098.

* cited by examiner

*Primary Examiner* — Alana Harris Dent
(74) *Attorney, Agent, or Firm* — Troutman Pepper Hamilton Sanders LLP (Rochester)

(57) ABSTRACT

There has been a recent shift in cancer therapy from one size fits all to a personalized and tailored treatment for individual patients to increase efficiency and avoid unnecessary toxicity. This invention relates to a method of determining the prognosis and suitable treatment of cancer in a subject by measuring the level of expression of SPAG5. In particular, it relates to a method where high expression of SPAG5 in tumour cells correlates with aggressive tumours.

8 Claims, 36 Drawing Sheets

MULTIVARIATE LOGISTIC REGRESSION MODEL FOR SPAG5 RNA EXPRESSION

Figure 1:
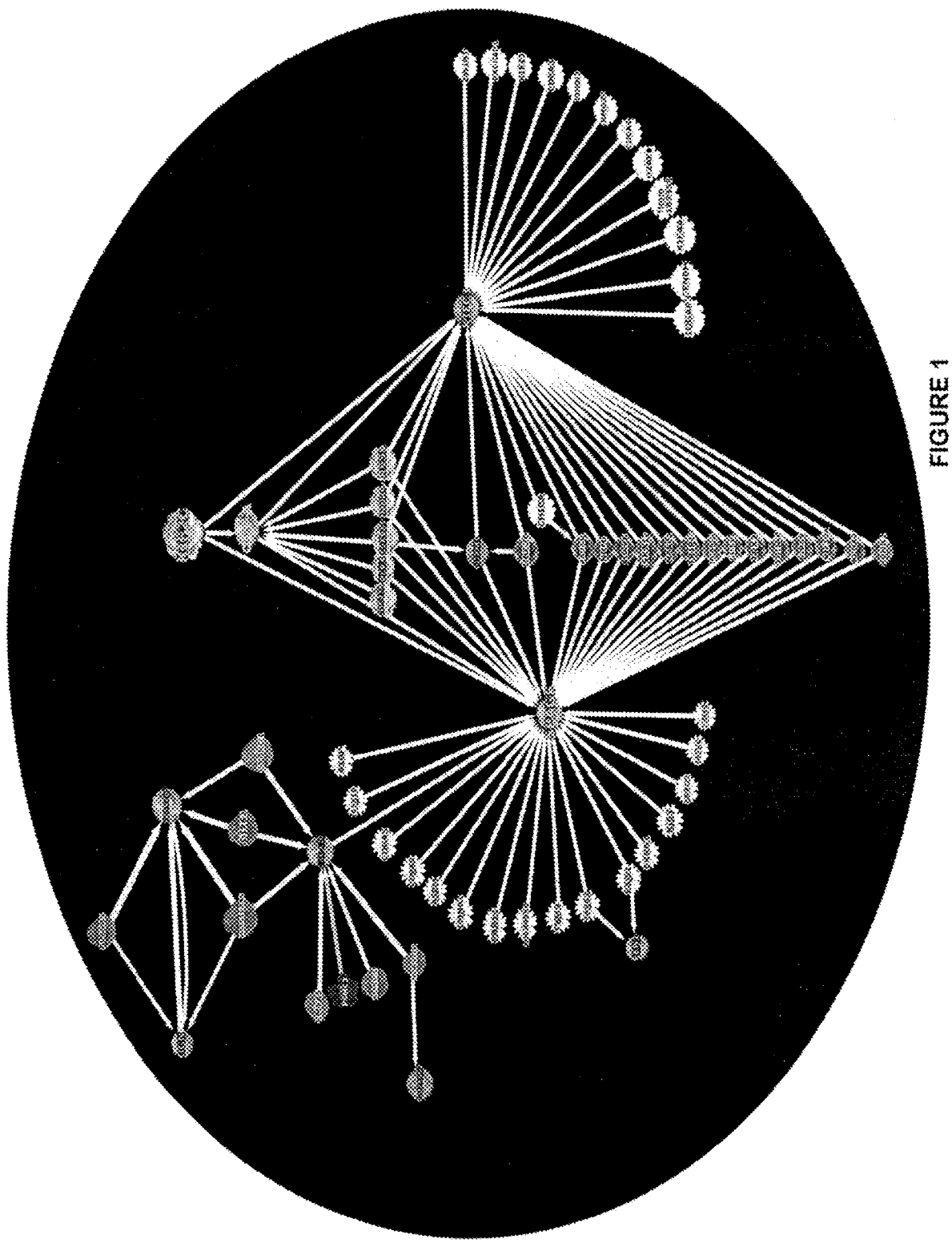

| Factors | OR | 95% CI | p |
|---|---|---|---|
| ER (+) | 0.2 | (0.150-0.52) | 0.005 |
| Mitosis | 5.4 | (2.8-10.6) | 0.000007 |

FIGURE 3

Multivariate logistic regression model for SPAG5 protein expression

| Factors | OR | 95% CI | p |
|---|---|---|---|
| ER (+) | 0.27 | (0.18-0.41) | 0.000000006 |
| Mitosis | 1.59 | (1.2-2.1) | 0.0005 |
| P16 mutation | 2.22 | (1.4-3.5) | 0.001 |

FIGURE 10

Multivariate analysis confirm Top2A protein as an independent predictor for pCR

| Factors | OR | 95% CI | P |
|---|---|---|---|
| SPAG5 (+) | 2.5 | (1.6–3.9) | <0.000001 |
| TOP2A | 6.8 | (1.3–35.6) | 0.02 |

FIGURE 14

Clinico-pathological correlations of SPAG5 protein expression in both the Training and Test sets

| Variables | Training Set (n=) n (%) | | p value | Test Set (n=) | | p value |
|---|---|---|---|---|---|---|
| | SPAG5 negative (n=) | SPAG5 positive (n=) | | SPAG5 negative (n=) | SPAG5 positive (n=) | |
| Pathological Parameters: | | | | | | |
| Tumour size<br>T1 a+b (=<1.0)<br>T1 c (>1.0-2.0)<br>T2 (>2.0-5.0)<br>T3 (>5) | 63(11.5)<br>292(53.1)<br>179(32.5)<br>16(2.9) | 14(9.8)<br>69(48.3)<br>54(37.8)<br>6(4.2) | 0.512 | 74(13.3)<br>274(49.4)<br>196(35.3)<br>11(2.0) | 7(5)<br>68(48.9)<br>62(44.6)<br>2(1.4) | 0.025 |
| Lymph node stage<br>Negative<br>Positive (1-3 nodes)<br>Positive (>3 nodes) | 340(61.7)<br>159(28.9)<br>52(9.4) | 88(61.5)<br>42(29.4)<br>13(9.1) | 0.987 | 355(63.7)<br>155(27.8)<br>47(8.4) | 70(50.0)<br>60(42.9)<br>10(7.1) | 0.003 |
| Tumour grade<br>G1<br>G2<br>G3 | 113(20.5)<br>210(38.2)<br>227(41.3) | 13(9.1)<br>26(18.2)<br>104(72.7) | 0.001 | 112(20.2)<br>221(39.8)<br>222(40.0) | 7(5.0)<br>24(17.3)<br>108(77.7) | 0.001 |
| Mitotic index<br>M1 (low; mitoses <10)<br>M2 (medium; mitoses 10-18)<br>M3 (high; mitoses >18) | 233(42.7)<br>110(20.1)<br>203(37.2) | 24(17.1)<br>18(12.9)<br>98(70.0) | 0.001 | 234(42.5)<br>117(21.3)<br>199(36.2) | 16(11.6)<br>18(13.0)<br>104(75.4) | 0.001 |
| Pleomorphism<br>P1<br>P2<br>P3 | 19(3.5)<br>251(46)<br>276(50.5) | 2(1.4)<br>23(16.4)<br>115(82.1) | 0.001 | 14(2.5)<br>268(48.7)<br>268(48.7) | 1(0.7)<br>26(18.8)<br>111(80.4) | 0.001 |
| Tubule Formation<br>T1<br>T2<br>T3 | 34(6.2)<br>197(36.1)<br>315(57.7) | 1(0.7)<br>39(27.9)<br>100(71.4) | 0.002 | 37(6.7)<br>198(36.0)<br>315(57.3) | 2(1.4)<br>31(22.5)<br>105(76.1) | 0.001 |
| Tumour type<br>IDC-NST<br>Medullary/Atypical<br>Tubular Carcinoma<br>Invasive lobular carcinoma<br>Others | 258(54.2)<br>6(1.3)<br>112(23.5)<br>61(12.8)<br>39(8.2) | 96(75.6)<br>8(6.3)<br>17(13.4)<br>4(3.1)<br>2(1.6) | 0.001 | 250(52.1)<br>4(0.8)<br>110(22.9)<br>57(11.9)<br>59(12.3) | 89(70.1)<br>13(10.2)<br>13(10.2)<br>4(3.1)<br>8(6.3) | 0.001 |
| Lymphovascular Invasion<br>Yes<br>No | 173(31.7)<br>373(68.3) | 52(37.4)<br>87(62.6) | 0.199 | 170(31.1)<br>376(68.9) | 44(31.7)<br>95(68.3) | 0.906 |
| Hormonal receptors: | | | | | | |
| Oestrogen receptor<br>Negative<br>Positive | 107(19.6)<br>438(80.4) | 80(57.6)<br>59(42.4) | 0.001 | 95(17.4)<br>452(82.6) | 67(48.6)<br>71(51.4) | 0.001 |
| Progesterone receptor<br>Negative<br>Positive | 187(36.5)<br>325(63.5) | 83(62.9)<br>49(37.1) | 0.001 | 173(33.5)<br>344(66.5) | 79(59.0)<br>55(41.0) | 0.001 |
| Androgen receptor<br>Negative<br>Positive | 135(31.2)<br>298(68.8) | 66(59.5)<br>45(40.5) | 0.001 | 127(29.3)<br>306(70.7) | 73(61.9)<br>45(38.1) | 0.001 |

Figure 22

| HER2 Family | | | | | | |
|---|---|---|---|---|---|---|
| EGFR<br>Negative<br>Overexpression | 340(80.4)<br>83(19.6) | 80(68.4)<br>37(31.6) | 0.006 | 367(85.7)<br>61(14.3) | 83(70.9)<br>34(29.1) | 0.001 |
| HER2<br>Negative<br>Overexpression | 489(90.1)<br>54(9.9) | 124(88.6)<br>16(11.4) | 0.606 | 481(88.6)<br>62(11.4) | 117(84.2)<br>22(15.8) | 0.158 |
| HER3<br>Negative<br>Overexpression | 214(50.2)<br>212(49.8) | 56(48.7)<br>59(51.3) | 0.770 | 235(52.7)<br>211(47.3) | 55(47.8)<br>60(52.2) | 0.352 |
| HER4<br>Negative<br>Overexpression | 205(46.9)<br>232(53.1) | 52(45.2)<br>63(54.8) | 0.746 | 194(43.4)<br>253(56.6) | 46(41.1)<br>66(58.9) | 0.656 |
| P53/apoptosis pathways: | | | | | | |
| P53<br>Negative<br>positive | 383(86.5)<br>60(13.5) | 77(65.3)<br>41(34.7) | 0.001 | 371(85.10<br>65(14.9) | 76(62.3)<br>46(37.7) | 0.001 |
| P21<br>Negative<br>positive | 218(55.9)<br>172(44.1) | 74(63.8)<br>42(36.2) | 0.131 | 213(51.8)<br>198(48.2) | 79(65.8)<br>41(34.2) | 0.007 |
| MDM4<br>Negative<br>Overexpression | 271(83.1)<br>55(16.9) | 82(83.7)<br>16(16.3) | 0.899 | 283(82.5)<br>60(17.5) | 94(91.3)<br>9(8.7) | 0.031 |
| MDM2<br>Negative<br>Overexpression | 267(70.3)<br>113(29.7) | 95(85.6)<br>16(14.4) | 0.001 | 281(72.6)<br>106(27.4) | 101(88.6)<br>13(11.4) | 0.001 |
| Bcl2<br>Negative<br>Positive | 137(27.6)<br>360(72.4) | 70(53.0)<br>62(47.0) | 0.001 | 153(30.5)<br>348(69.5) | 67(51.5)<br>63(48.5) | 0.001 |
| Bax<br>Negative<br>Positive | 226(70.6)<br>94(29.4) | 60(65.2)<br>32(34.8) | 0.321 | 240(72.5)<br>91(27.5) | 60(64.5)<br>33(35.5) | 0.134 |
| Proliferation/Cell cycle regulatory proteins | | | | | | |
| MIB1<br>Negative<br>Positive | 175(39.5)<br>268(60.5) | 23(19.8)<br>93(80.2) | 0.001 | 201(43.5)<br>261(56.5) | 20(16.7)<br>100(83.3) | 0.001 |
| TOP2A<br>Negative<br>Positive | 195(48.3)<br>209(51.7) | 47(43.5)<br>61(56.5) | 0.380 | 193(47.8)<br>211(52.2) | 50(45.0)<br>61(55.0) | 0.610 |
| KIF2C<br>Negative<br>Positive | 161(42)<br>222(58.0) | 27(27.8)<br>70(72.2) | 0.010 | 166(41.5)<br>234(58.5) | 20(19.4)<br>83(80.6) | 0.001 |

Figure 22 - Continued

| | | | | | | |
|---|---|---|---|---|---|---|
| Cycline B2<br>Negative<br>Positive | 282(53.7)<br>243(46.3) | 44(33.3)<br>88(66.7) | 0.001 | 278(53.9)<br>238(46.1) | 59(45.7)<br>70(54.3) | 0.098 |
| P27<br>Negative<br>Positive | 202(57.5)<br>149(42.5) | 62(65.3)<br>33(34.7) | 0.175 | 198(57.6)<br>146(42.4) | 65(67.7)<br>37(32.3) | 0.073 |
| P16<br>Negative<br>Positive | 346(90.8)<br>35(9.2) | 78(70.3)<br>33(29.7) | 0.001 | 357(92.7)<br>28(7.3) | 77(66.4)<br>39(33.6) | 0.001 |
| DNA repair genes | | | | | | |
| ATM<br>Negative<br>Positive | 151(46.7)<br>172(53.3) | 53(59.6)<br>36(40.4) | 0.032 | 169(51.4)<br>160(48.6) | 51(56.7)<br>39(43.3) | 0.372 |
| BRCA1<br>Negative<br>Positive | 52(14.1)<br>318(85.9) | 25(23.4)<br>82(76.6) | 0.021 | 68(17.4)<br>322(82.6) | 33(30.6)<br>75(69.4) | 0.003 |
| XRCC1<br>Low<br>High | 71(15.4)<br>389(84.6) | 32(25.6)<br>93(74.4) | 0.008 | 55(11.6)<br>418(88.4) | 26(21.8)<br>93(78.2) | 0.004 |
| SMUG1<br>Low<br>High | 91(23.9)<br>290(76.1) | 31(31.6)<br>67(68.4) | 0.116 | 87(21.1)<br>325(78.9) | 43(41.3)<br>61(58.7) | 0.001 |
| FEN1<br>Low<br>High | 230(53.5)<br>200(46.5) | 63(53.4)<br>55(46.6) | 0.985 | 242(54.0)<br>206(46.0) | 55(49.0)<br>57(50.9) | 0.352 |
| Cytokeratin | | | | | | |
| CK19<br>Negative<br>Positive | 20(4.4)<br>436(95.6) | 13(10.4)<br>112(89.6) | 0.010 | 21(4.6)<br>436(95.4) | 19(15.2)<br>106(84.8) | 0.001 |
| CK18<br>Negative<br>Positive | 39(9.2)<br>387(90.8) | 28(23.7)<br>90(76.3) | 0.001 | 23(5.3)<br>410(94.7) | 26(22.8)<br>88(77.2) | 0.001 |
| CK5/6<br>Negative<br>Positive | 398(86.9)<br>60(13.1) | 80(63.5)<br>46(36.5) | 0.001 | 412(89.2)<br>50(10.8) | 93(75.6)<br>30(24.4) | 0.001 |
| CK14<br>Negative<br>Positive | 406(89.4)<br>48(10.6) | 101(80.8)<br>24(19.2) | 0.010 | 401(88.1)<br>54(11.9) | 109(86.5)<br>17(13.5) | 0.622 |
| Epithelial Mesenchymal transition | | | | | | |
| Vimentin<br>Negative<br>Positive | 281(92.7)<br>22(7.3) | 64(73.6)<br>23(26.4) | 0.001 | 449(98.2)<br>8(1.8) | 115(93.5)<br>8(6.5) | 0.004 |

Figure 22 - Continued

| | | | | | | |
|---|---|---|---|---|---|---|
| P63<br>Negative<br>Positive | 447(99.6)<br>2(0.4) | 122(98.4)<br>2(1.6) | 0.167 | 308(94.5)<br>18(5.5) | 66(68.8)<br>30(31.3) | 0.001 |
| SMA<br>Negative<br>Positive | 395(88.6)<br>51(11.4) | 101(82.8)<br>21(17.2) | 0.089 | 408(89.3)<br>49(10.7) | 96(78.0)<br>27(22.0) | 0.001 |
| E-cadherin<br>Negative<br>Positive | 23(5.1)<br>431(94.9) | 13(11.2)<br>103(88.8) | 0.015 | 29(6.4)<br>424(93.6) | 6(4.9)<br>117(95.1) | 0.530 |
| Triple Negative phenotype<br>No<br>Yes | 477(88.7)<br>61(11.3) | 71(52.6)<br>64(47.4) | 0.001 | 490(90.4)<br>52(9.6) | 86(61.9)<br>53(38.1) | 0.001 |
| Basal like phenotype<br>No<br>Yes | 488(92.2)<br>41(7.8) | 86(66.2)<br>44(33.8) | 0.001 | 504(94.7)<br>28(5.3) | 101(74.8)<br>34(25.2) | 0.001 |

Figure 22 - Continued

Comparison between the clinico-pathological characteristics of the Training and Validation sets showing both sets were well balanced

| Variable | | Training Set n (%) | Validation Set n (%) | p value |
|---|---|---|---|---|
| Pathological Parameters: | | | | |
| SPAG5 expression | Positive<br>Negative | 559(79.9)<br>141(20.1) | 557(79.6)<br>143(20.4) | 0.894 |
| Tumour size | T1 a+ b (=<1.0)<br>T1 c (>1.0-2.0)<br>T2 (>2.0-5.0)<br>T3 (>5) | 77(11.1)<br>358(51.7)<br>236(34.1)<br>21(3.0) | 81(11.7)<br>345(49.6)<br>255(36.7)<br>14(2.0) | 0.481 |
| Lymph node stage | Negative<br>Positive (1-3 nodes)<br>Positive (>3 nodes) | 433(62.4)<br>201(29)<br>60(8.6) | 420(60.3)<br>215(30.8)<br>62(8.9) | 0.706 |
| Tumour grade | Low grade (G1)<br>Intermediate grade (G2)<br>High grade (G3) | 125(18.1)<br>242(35)<br>325(47) | 120(17.3)<br>239(34.4)<br>336(48.3) | 0.862 |
| Lymphovascular invasion | No<br>Yes | 468(68.1)<br>219(31.9) | 463(67.8)<br>220(32.2) | 0.895 |
| Tumour type | IDC-NST<br>Medullary<br>Tubular<br>Lobular<br>Others | 349(58.1)<br>11(1.8)<br>130(21.6)<br>67(11.1)<br>44(7.3) | 344(56.5)<br>20(3.3)<br>122(20.0)<br>59(9.7)<br>64(10.5) | 0.133 |
| Mitotic index | M1 (low; mitoses <10)<br>M2 (medium; mitoses 10-18)<br>M3 (high; mitoses >18) | 259(37.8)<br>130(19)<br>296(43.2) | 248(36)<br>133(19.3)<br>308(44.7) | 0.779 |
| Bilateral phenotype | Unilateral<br>Bilateral | 577(94.9)<br>31(5.1) | 585(95.9)<br>25(4.1) | 0.405 |
| Oestrogen receptor | Negative<br>Positive | 174(25.4)<br>510(74.6) | 175(25.5)<br>510(74.5) | 0.963 |
| HER2 receptor | Negative<br>Overexpression | 612(89.5)<br>72(10.5) | 599(88.0)<br>82(12.0) | 0.376 |
| Basal Like | No<br>Yes | 584(88.8)<br>74(11.2) | 595(89.1)<br>73(10.9) | 0.854 |
| Triple Negative | No<br>Yes | 561(83.4)<br>112(16.6) | 563(82.7)<br>118(17.3) | 0.737 |
| Treatments: | | | | |
| Chemotherapy | No chemotherapy<br>Received CMF<br>Anthracycline | 563(85.2)<br>97(14.7)<br>1(0.2) | 564(85.6)<br>95(14.4)<br>0(0.0) | 0.601 |

Figure 23

| | | | | | |
|---|---|---|---|---|---|
| Endocrine therapy | No<br>Tamoxifen<br>Tamoxifen+Zoladex<br>Others | 408(60.9)<br>233(34.8)<br>22(3.3)<br>2(0.3) | 396(59.9)<br>231(34.9)<br>25(3.8)<br>5(0.8) | 0.684 |
| Clinical features: | | | | |
| Family history | No<br>Yes | 445(77.8)<br>127(22.2) | 448(76.5)<br>138(23.5) | 0.585 |
| Recurrence | Yes<br>No<br>Unknown | 396(57.2)<br>296(42.8) | 413(59.6)<br>280(40.4) | 0.371 |
| Distant Metastases | Yes<br>No<br>Unknown | 467(67.5)<br>225(32.5) | 483(69.7)<br>210(30.3) | 0.375 |
| NPI prognostic groups (PG)<br>Excellent PG<br>Good PG<br>Moderate I PG<br>Moderate II PG<br>Poor PG<br>Very poor PG<br>Unknown | (2.08-2.40)<br>(2.42-3.40)<br>(3.42-4.40)<br>(4.42-5.40)<br>(5.42-6.49)<br>(≥6.50) | 77(11.1)<br>162(23.4)<br>218(31.5)<br>141(20.4)<br>69(10.0)<br>24(3.5)<br>0(0.0) | 77(11.1)<br>152(21.9)<br>204(29.4)<br>166(23.9)<br>72(10.4)<br>22(3.2)<br>2(0.3) | 0.549 |

Figure 23 continued

| | Input Index | ATE | P-value | Rank | Gene Symbol | Gene Title | Entrez Gene ID | Cytoband |
|---|---|---|---|---|---|---|---|---|
| 218009_s_at | 17913 | 0.068037 | 4.48793E-05 | 1 | PRC1 | protein regulator of cytokinesis 1 | 9055 | 15q26.1 |
| 202954_at | 3023 | 0.070585 | 8.97585E-05 | 2 | UBE2C | ubiquitin-conjugating enzyme E2C | 11065 | 20q13.12 |
| 205046_at | 5112 | 0.074025 | 0.000134638 | 3 | CENPE | centromere protein E, 312kDa | 1062 | 4q24-q25 |
| 209773_s_at | 9800 | 0.074931 | 0.000179517 | 4 | RRM2 | ribonucleotide reductase M2 | 6241 | 2p25-p24 |
| 209680_s_at | 9707 | 0.074925 | 0.000224396 | 5 | KIF2C | kinesin family member C1 | 3833 | 6p21.3 |
| 209408_at | 9440 | 0.07608 | 0.000269276 | 6 | KIF2C | kinesin family member 2C | 11004 | 1p34.1 |
| 218039_at | 17943 | 0.076182 | 0.000314155 | 7 | NUSAP1 | nucleolar and spindle associated protein 1 | 51203 | 15q15.1 |
| 222039_at | 21938 | 0.077106 | 0.000359034 | 8 | KIF18B | kinesin family member 18B | 146909 | 17q21.31 |
| 202095_s_at | 2164 | 0.078634 | 0.000403913 | 9 | BIRC5 | baculoviral IAP repeat containing 5 | 332 | 17q25 |
| 210559_s_at | 10566 | 0.07905 | 0.000448793 | 10 | CDK1 | cyclin-dependent kinase 1 | 983 | 10q21.1 |
| 210052_s_at | 10076 | 0.07927 | 0.000493672 | 11 | TPX2 | TPX2, microtubule-associated, homolog (Xenopus laevis) | 22974 | 20q11.2 |
| 203214_x_at | 3281 | 0.079574 | 0.000538551 | 12 | CDK1 | cyclin-dependent kinase 1 | 983 | 10q21.1 |
| 204026_s_at | 4092 | 0.079579 | 0.000583431 | 13 | ZWINT | ZW10 interactor | 11130 | 10q21-q22 |
| 201292_at | 1361 | 0.079804 | 0.00062831 | 14 | TOP2A | topoisomerase (DNA) II alpha 170kDa | 7153 | 17q21-q22 |
| 201291_s_at | 1360 | 0.079945 | 0.000673189 | 15 | TOP2A | topoisomerase (DNA) II alpha 170kDa | 7153 | 17q21-q22 |
| 202503_s_at | 2572 | 0.080936 | 0.000718068 | 16 | KIAA0101 | KIAA0101 | 9768 | 15q22.31 |
| 204092_s_at | 4158 | 0.081948 | 0.000762948 | 17 | AURKA | aurora kinase A | 6790 | 20q13 |
| 202870_s_at | 2939 | 0.08196 | 0.000807827 | 18 | CDC20 | cell division cycle 20 homolog (S. cerevisiae) | 991 | 1p34.1 |
| 207828_s_at | 7886 | 0.082351 | 0.000852706 | 19 | CENPF | centromere protein F, 350/400kDa (mitosin) | 1063 | 1q32-q41 |
| 218726_at | 18629 | 0.082456 | 0.000897585 | 20 | HJURP | Holliday junction recognition protein | 55355 | 2q37.1 |
| 38158_at | 260 | 0.082684 | 0.000942465 | 21 | ESPL1 | extra spindle pole bodies homolog 1 (S. cerevisiae) | 9700 | 12q |
| 203705_at | 2774 | 0.083253 | 0.000987344 | 22 | CCNB2 | cyclin B2 | 9133 | 15q22.2 |
| 222077_s_at | 21976 | 0.083613 | 0.001032223 | 23 | RACGAP1 | Rac GTPase activating protein 1 | 29127 | 12q13.12 |
| 208079_s_at | 8127 | 0.083817 | 0.001077103 | 24 | AURKA | aurora kinase A | 6790 | 20q13 |
| 201890_at | 1959 | 0.084305 | 0.001121982 | 25 | RRM2 | ribonucleotide reductase M2 | 6241 | 2p25-p24 |
| 203554_x_at | 3620 | 0.084285 | 0.001166861 | 26 | PTTG1 | pituitary tumor-transforming 1 | 9232 | 5q35.1 |
| 202580_x_at | 2649 | 0.084501 | 0.001211174 | 27 | FOXM1 | forkhead box M1 | 2305 | 12p13 |
| 214710_s_at | 14625 | 0.084945 | 0.00125662 | 28 | CCNB1 | cyclin B1 | 891 | 5q12 |
| 203764_at | 3830 | 0.085177 | 0.001301499 | 29 | DLGAP5 | discs, large (Drosophila) homolog-associated protein 5 | 9787 | 14q22.3 |
| 203213_at | 3280 | 0.08537 | 0.001346378 | 30 | CDK1 | cyclin-dependent kinase 1 | 983 | 10q21.1 |
| 204444_at | 4510 | 0.085585 | 0.001391258 | 31 | KIF11 | kinesin family member 11 | 3832 | 10q24.1 |
| 204033_at | 4099 | 0.085774 | 0.001436137 | 32 | TRIP13 | thyroid hormone receptor interactor 13 | 9319 | 5p15.33 |
| 203022_at | 3091 | 0.086316 | 0.001481016 | 33 | RNASEH2A | ribonuclease H2, subunit A | 10535 | 19p13.2 |
| 218542_at | 18446 | 0.086394 | 0.001525895 | 34 | CEP55 | centrosomal protein 55kDa | 55165 | 10q23.33 |
| 203046_s_at | 3115 | 0.086787 | 0.001570775 | 35 | TIMELESS | timeless homolog (Drosophila) | 8914 | 12q13.3 |
| 218115_at | 18019 | 0.086851 | 0.001615654 | 36 | ASF1B | ASF1 anti-silencing function 1 homolog B (S. cerevisiae) | 55723 | 19p13.12 |
| 204817_at | 4883 | 0.086903 | 0.001660533 | 37 | ESPL1 | extra spindle pole bodies homolog 1 (S. cerevisiae) | 9700 | 12q |
| 213008_at | 12939 | 0.087011 | 0.001705412 | 38 | FANCI | Fanconi anemia, complementation group I | 55215 | 15q26.1 |
| 204641_at | 4707 | 0.087019 | 0.001750292 | 39 | NEK2 | NIMA (never in mitosis gene a)-related kinase 2 | 4751 | 1q32.2-q41 |
| 203362_s_at | 3428 | 0.087335 | 0.001795171 | 40 | MAD2L1 | MAD2 mitotic arrest deficient-like 1 (yeast) | 4085 | 4q27 |

Figure 24

| Probe | | | Gene Symbol | Gene Name | Entrez ID | Cytoband |
|---|---|---|---|---|---|---|
| 204162_at | 4228 | 0.087354 | 0.001184005 | 41 NDC80 | NDC80 kinetochore complex component homolog (S. cerevisiae) | 10403 | 18p11.32 |
| 204962_s_at | 5028 | 0.087898 | 0.001188493 | 42 C2orf18 /// CENPA | chromosome 2 open reading frame 18 /// centromere protein A | 1058 /// 54978 | 2p23.3 /// 3p24-p21 |
| 218309_at | 18212 | 0.08791 | 0.001929809 | 43 TACC3 | transforming, acidic coiled-coil containing protein 3 | 10460 | 4p16.3 |
| 207165_at | 7230 | 0.08871 | 0.001974588 | 44 HMMR | hyaluronan-mediated motility receptor (RHAMM) | 3161 | 5q33.2-qter |
| 221520_s_at | 21422 | 0.089173 | 0.002019367 | 45 CDCA8 | cell division cycle associated 8 | 55143 | 1p34.3 |
| 213007_at | 12929 | 0.089644 | 0.002064447 | 46 FANCI | Fanconi anemia, complementation group I | 55215 | 15q26.1 |
| 219918_s_at | 19821 | 0.090307 | 0.002109326 | 47 ASPM | asp (abnormal spindle) homolog, microcephaly associated (Drosophila) | 259266 | 1q31 |
| 203755_at | 3821 | 0.090496 | 0.002154205 | 48 BUB1B | budding uninhibited by benzimidazoles 1 homolog beta (yeast) | 701 | 15q15 |
| 212949_at | 12871 | 0.090644 | 0.002199084 | 49 NCAPH | non-SMC condensin I complex, subunit H | 23397 | 2q11.2 |
| 220651_s_at | 20554 | 0.090678 | 0.002243564 | 50 MCM10 | minichromosome maintenance complex component 10 | 55388 | 10p13 |
| 209714_s_at | 9741 | 0.090093 | 0.002288843 | 51 CDKN3 | cyclin-dependent kinase inhibitor 3 | 1033 | 14q22 |
| 218755_at | 18656 | 0.091448 | 0.002333722 | 52 KIF20A | kinesin family member 20A | 10112 | 5q31 |
| 209542_at | 9670 | 0.091476 | 0.002378602 | 53 BUB1 | budding uninhibited by benzimidazoles 1 homolog (yeast) | 699 | 2q14 |
| 218355_at | 18259 | 0.09171 | 0.002423481 | 54 KIF4A | kinesin family member 4A | 24137 | Xq13.1 |
| 203342_at | 3408 | 0.091949 | 0.002468336 | 55 TIMM17B | translocase of inner mitochondrial membrane 17 homolog B (yeast) | 10245 | Xp11.23 |
| 204825_at | 4891 | 0.092189 | 0.002513239 | 56 MELK | maternal embryonic leucine zipper kinase | 9833 | 9p13.2 |
| 206364_at | 6429 | 0.092493 | 0.002558129 | 57 KIF14 | kinesin family member 14 | 9928 | 1q32.1 |
| 203432_at | 3498 | 0.092697 | 0.002602998 | 58 TMPO | thymopoietin | 7112 | 12q22 |
| 218883_s_at | 18786 | 0.092773 | 0.002647877 | 59 MLF1IP | MLF1 interacting protein | 79682 | 4q35.1 |
| 204146_at | 4212 | 0.092889 | 0.002692756 | 60 RAD51AP1 | RAD51 associated protein 1 | 10635 | 12p13.2-p13.1 |
| 202094_at | 2163 | 0.092986 | 0.002737636 | 61 BIRC5 | baculoviral IAP repeat containing 5 | 332 | 17q25 |
| 204170_s_at | 4236 | 0.093013 | 0.002782515 | 62 CKS2 | CDC28 protein kinase regulatory subunit 2 | 1164 | 9q22 |
| 213011_s_at | 12933 | 0.093387 | 0.002827394 | 63 TPI1 | triosephosphate isomerase 1 | 7167 | 12p13 |
| 201584_s_at | 1953 | 0.093738 | 0.002872274 | 64 DDX39A | DEAD (Asp-Glu-Ala-Asp) box polypeptide 39A | 10212 | 19p13.12 |
| 202779_s_at | 2848 | 0.093776 | 0.002917153 | 65 UBE2S | ubiquitin-conjugating enzyme E2S | 27338 | 19q13.43 |
| 221069_s_at | 20971 | 0.093949 | 0.002962032 | 66 TACO1 | translational activator of mitochondrially encoded cytochrome c oxidase I | 51204 | 17q23.3 |
| 224436_s_at | 21338 | 0.094049 | 0.003006911 | 67 CDCA3 | cell division cycle associated 3 | 83461 | 12p13 |
| 205034_at | 5100 | 0.094375 | 0.003051791 | 68 CCNE2 | cyclin E2 | 9134 | 8q22.1 |
| 201088_at | 1157 | 0.094618 | 0.003099667 | 69 KPNA2 | karyopherin alpha 2 (RAG cohort 1, importin alpha 1) | 3838 | 17q24.2 |
| 219650_at | 19553 | 0.095059 | 0.003141549 | 70 ERCC6L | excision repair cross-complementing rodent repair deficiency, complementation group 6-like | 54821 | Xq13.1 |
| 221258_s_at | 21160 | 0.095063 | 0.003186429 | 71 KIF18A | kinesin family member 18A | 81930 | 11p14.1 |
| 202338_at | 2407 | 0.095063 | 0.003231308 | 72 TK1 | thymidine kinase 1, soluble | 7083 | 17q23.2-q25.3 |
| 204822_at | 4888 | 0.09561 | 0.003276187 | 73 TTK | TTK protein kinase | 7272 | 6q13-q21 |
| 221521_s_at | 21423 | 0.095753 | 0.003321066 | 74 GINS2 | GINS complex subunit 2 (Psf2 homolog) | 51659 | 16q24.1 |
| 202107_s_at | 2176 | 0.095796 | 0.003365946 | 75 MCM2 | minichromosome maintenance complex component 2 | 4171 | 3q21 |
| 218741_at | 18644 | 0.096035 | 0.003410825 | 76 CENPM | centromere protein M | 79019 | 22q13.2 |
| 209916_at | 9941 | 0.09605 | 0.003455704 | 77 DHTKD1 | dehydrogenase E1 and transketolase domain containing 1 | 55526 | 10p14 |
| 221970_s_at | 21869 | 0.096471 | 0.003500583 | 78 NOL11 | nucleolar protein 11 | 25926 | 17q24.2 |

Figure 24 - Continued

| Probe ID | | | Gene | Description | | Cytoband |
|---|---|---|---|---|---|---|
| 206102_at | 6167 | 0.096646 | 0.003545463 | 79 GINS1 | GINS complex subunit 1 (Psf1 homolog) | 9837 | 20p11.21 |
| 218662_s_at | 18555 | 0.096662 | 0.003590342 | 80 NCAPG | non-SMC condensin I complex, subunit G | 64151 | 4p15.33 |
| 213599_at | 13518 | 0.096769 | 0.003635221 | 81 OIP5 | Opa interacting protein 5 | 11339 | 15q15.1 |
| 205024_s_at | 5090 | 0.096786 | 0.003680101 | 82 RAD51 | RAD51 homolog (S. cerevisiae) | 5888 | 15q15.1 |
| 212832_s_at | 127564 | 0.096988 | 0.003724498 | 83 CKAP5 | cytoskeleton associated protein 5 | 9793 | 11p11.2 |
| 202589_at | 2658 | 0.097109 | 0.003769859 | 84 TYMS | thymidylate synthetase | 7298 | 18p11.32 |
| 200830_at | 899 | 0.097284 | 0.003814738 | 85 PSMD2 | proteasome (prosome, macropain) 26S subunit, non-ATPase, 2 | 5708 | 3q27.1 |
| 205436_s_at | 5502 | 0.097436 | 0.003859618 | 86 H2AFX | H2A histone family, member X | 3014 | 11q23.3 |
| 208870_x_at | 8904 | 0.097755 | 0.003904497 | 87 ATP5C1 | ATP synthase, H+ transporting, mitochondrial F1 complex, gamma polypeptide 1 | 509 | 10p15.1 |
| 204768_s_at | 4834 | 0.097794 | 0.003949376 | 88 FEN1 | flap structure-specific endonuclease 1 | 2237 | 11q12 |
| 212022_s_at | 11947 | 0.097815 | 0.003994255 | 89 MKI67 | antigen identified by monoclonal antibody Ki-67 | 4288 | 10q26.2 |
| 211762_s_at | 11700 | 0.097874 | 0.004039135 | 90 KPNA2 | karyopherin alpha 2 (RAG cohort 1, importin alpha 1) | 3838 | 17q24.2 |
| 219757_s_at | 19690 | 0.098013 | 0.004084014 | 91 ECT2 | epithelial cell transforming sequence 2 oncogene | 1894 | 3q26.1-q26.2 |
| 213059_at | 13030 | 0.098308 | 0.004128893 | 92 DNAJC9 | DnaJ (Hsp40) homolog, subfamily C, member 9 | 23234 | 10q22.2 |
| 213175_s_at | 13096 | 0.098218 | 0.004173773 | 93 SNRPB | small nuclear ribonucleoprotein polypeptides B and B1 | 6628 | 20p13 |
| 212279_at | 12204 | 0.098456 | 0.004218652 | 94 TMEM97 | transmembrane protein 97 | 27346 | 17q11.2 |
| 217938_s_at | 17842 | 0.098469 | 0.004263531 | 95 KCMF1 | potassium channel modulatory factor 1 | 56888 | 2p11.2 |
| 217835_x_at | 17739 | 0.098476 | 0.004308441 | 96 C20orf24 ///TGIF2-C20ORF24 | chromosome 20 open reading frame 24 /// TGIF2-C20orf24 readthrough | 100527943 /// 55969 | 20q /// 20q11.23 |
| 212570_at | 12594 | 0.098856 | 0.004353329 | 97 ELN | elastin | 2006 | 7q11.23 |
| 200822_x_at | 891 | 0.098748 | 0.004398169 | 98 TPI1 | triosephosphate isomerase 1 | 7167 | 12p13 |
| 203967_at | 4033 | 0.098884 | 0.004443048 | 99 CDC6 | cell division cycle 6 homolog (S. cerevisiae) | 990 | 17q21.3 |
| 202233_s_at | 2302 | 0.098847 | 0.004487927 | 100 UQCRH /// UQCRHL | ubiquinol-cytochrome c reductase hinge protein /// ubiquinol-cytochrome c reductase hinge protein-like | 440567 /// 7388 | 1p34.1 /// 1p36.21 |

Figure 24 - Continued

| Input ID | Input Index | P-value | Average test error | Rank | Gene Symbol | Gene Title |
|---|---|---|---|---|---|---|
| 202954_at | 3023 | 4.5E-05 | 0.0653282 | 1 | UBE2C | ubiquitin-conjugating enzyme E2C |
| 218009_s_at | 17913 | 9E-05 | 0.0683053 | 2 | PRC1 | protein regulator of cytokinesis 1 |
| 209408_at | 9440 | 0.00013 | 0.0695952 | 3 | KIF2C | kinesin family member 2C |
| 202705_at | 2774 | 0.00018 | 0.0729931 | 4 | CCNB2 | cyclin B2 |
| 218726_at | 18629 | 0.00022 | 0.0734466 | 5 | HJURP | Holliday junction recognition protein |
| 209773_s_at | 9800 | 0.00027 | 0.0748707 | 6 | RRM2 | ribonucleotide reductase M2 |
| 210559_s_at | 10566 | 0.00031 | 0.0749061 | 7 | CDK1 | cyclin-dependent kinase 1 |
| 202095_s_at | 2164 | 0.00036 | 0.075594 | 8 | BIRC5 | baculoviral IAP repeat containing 5 |
| 201890_at | 1959 | 0.0004 | 0.0756054 | 9 | RRM2 | ribonucleotide reductase M2 |
| 205046_at | 5112 | 0.00045 | 0.0756889 | 10 | CENPE | centromere protein E, 312kDa |
| 221520_s_at | 21422 | 0.00049 | 0.0760005 | 11 | CDCA8 | cell division cycle associated 8 |
| 222039_at | 21938 | 0.00054 | 0.0762519 | 12 | KIF18B | kinesin family member 18B |
| 222077_s_at | 21976 | 0.00058 | 0.0767171 | 13 | RACGAP1 | Rac GTPase activating protein 1 |
| 203554_x_at | 3620 | 0.00063 | 0.0769713 | 14 | PTTG1 | pituitary tumor-transforming 1 |
| 38158_at | 260 | 0.00067 | 0.0774044 | 15 | ESPL1 | extra spindle pole bodies homolog 1 (S. cerevisiae) |
| 210052_s_at | 10076 | 0.00072 | 0.0775029 | 16 | TPX2 | TPX2, microtubule-associated, homolog (Xenopus laevis) |
| 204026_s_at | 4092 | 0.00076 | 0.0776379 | 17 | ZWINT | ZW10 interactor |
| 203214_x_at | 3281 | 0.00081 | 0.0776701 | 18 | CDK1 | cyclin-dependent kinase 1 |
| 202870_s_at | 2939 | 0.00085 | 0.0777786 | 19 | CDC20 | cell division cycle 20 homolog (S. cerevisiae) |
| 204444_at | 4510 | 0.0009 | 0.0783428 | 20 | KIF11 | kinesin family member 11 |
| 202503_s_at | 2572 | 0.00094 | 0.0783918 | 21 | KIAA0101 | KIAA0101 |
| 201292_at | 1361 | 0.00099 | 0.078515 | 22 | TOP2A | topoisomerase (DNA) II alpha 170kDa |
| 208079_s_at | 8127 | 0.00103 | 0.0785711 | 23 | AURKA | aurora kinase A |
| 204092_s_at | 4158 | 0.00108 | 0.0788585 | 24 | AURKA | aurora kinase A |
| 204033_at | 4099 | 0.00112 | 0.0793399 | 25 | TRIP13 | thyroid hormone receptor interactor 13 |
| 203755_at | 3821 | 0.00117 | 0.0795754 | 26 | BUB1B | budding uninhibited by benzimidazoles 1 homolog beta (yeast) |
| 218039_at | 17943 | 0.00121 | 0.0795946 | 27 | NUSAP1 | nucleolar and spindle associated protein 1 |
| 209680_s_at | 9707 | 0.00126 | 0.0797478 | 28 | KIFC1 | kinesin family member C1 |
| 203213_at | 3280 | 0.0013 | 0.0802577 | 29 | CDK1 | cyclin-dependent kinase 1 |
| 218542_at | 18446 | 0.00135 | 0.0802805 | 30 | CEP55 | centrosomal protein 55kDa |
| 202580_x_at | 2649 | 0.00139 | 0.0809903 | 31 | FOXM1 | forkhead box M1 |
| 209642_at | 9670 | 0.00144 | 0.0812858 | 32 | BUB1 | budding uninhibited by benzimidazoles 1 homolog (yeast) |
| 214710_s_at | 14625 | 0.00148 | 0.0813444 | 33 | CCNB1 | cyclin B1 |
| 220651_s_at | 20554 | 0.00153 | 0.08136988 | 34 | MCM10 | minichromosome maintenance complex component 10 |
| 209714_s_at | 9741 | 0.00157 | 0.0819117 | 35 | CDKN3 | cyclin-dependent kinase inhibitor 3 |
| 203362_s_at | 3428 | 0.00162 | 0.0820303 | 36 | MAD2L1 | MAD2 mitotic arrest deficient-like 1 (yeast) |
| 218308_at | 18212 | 0.00166 | 0.082412 | 37 | TACC3 | transforming, acidic coiled-coil containing protein 3 |
| 213008_at | 12930 | 0.00171 | 0.0826103 | 38 | FANCI | Fanconi anemia, complementation group I |
| 206364_at | 6429 | 0.00175 | 0.082896 | 39 | KIF14 | kinesin family member 14 |
| 204962_s_at | 5028 | 0.0018 | 0.0831165 | 40 | C2orf18 /// CENPA | chromosome 2 open reading frame 18 /// centromere protein A |
| 212949_at | 12871 | 0.00184 | 0.0831674 | 41 | NCAPH | non-SMC condensin I complex, subunit H |

Figure 25

| Probe | ID | p-value | Symbol | Description |
|---|---|---|---|---|
| 204146_at | 4212 | 0.00188 | RAD51AP1 | RAD51 associated protein 1 |
| 205034_at | 5100 | 0.00193 | CCNE2 | cyclin E2 |
| 203022_at | 3091 | 0.00197 | RNASEH2A | ribonuclease H2, subunit A |
| 203046_s_at | 3115 | 0.00202 | TIMELESS | timeless homolog (Drosophila) |
| 219918_s_at | 19821 | 0.00206 | ASPM | asp (abnormal spindle) homolog, microcephaly associated (Drosophila) |
| 204817_at | 4883 | 0.00211 | ESPL1 | extra spindle pole bodies homolog 1 (S. cerevisiae) |
| 207828_s_at | 7886 | 0.00215 | CENPF | centromere protein F, 350/400kDa (mitosin) |
| 201584_s_at | 1653 | 0.0022 | DDX39A | DEAD (Asp-Glu-Ala-Asp) box polypeptide 39A |
| 204822_at | 4888 | 0.00224 | TTK | TTK protein kinase |
| 201088_at | 1157 | 0.00229 | KPNA2 | karyopherin alpha 2 (RAG cohort 1, importin alpha 1) |
| 204162_at | 4228 | 0.00233 | NDC80 | NDC80 kinetochore complex component homolog (S. cerevisiae) |
| 201291_s_at | 1360 | 0.00238 | TOP2A | topoisomerase (DNA) II alpha 170kDa |
| 203432_at | 3498 | 0.00242 | TMPO | thymopoietin |
| 203764_at | 3830 | 0.00247 | DLGAP5 | discs, large (Drosophila) homolog-associated protein 5 |
| 201930_at | 1999 | 0.00251 | MCM6 | minichromosome maintenance complex component 6 |
| 204641_at | 4707 | 0.00256 | NEK2 | NIMA (never in mitosis gene a)-related kinase 2 |
| 221436_s_at | 21338 | 0.0026 | CDCA3 | cell division cycle associated 3 |
| 202779_s_at | 2848 | 0.00265 | UBE2S | ubiquitin-conjugating enzyme E2S |
| 202233_s_at | 2302 | 0.00269 | UQCRH /// UQCRHL | ubiquinol-cytochrome c reductase hinge protein /// ubiquinol-cytochrome c reductase hinge protein-like |
| 205967_at | 6033 | 0.00274 | HIST1H4A /// HIST1H4B /// HIST1H4C /// HIST1H4D /// HIST1H4E /// HIST1H4F /// HIST1H4H /// HIST1H4I /// HIST1H4J /// HIST1H4K /// HIST1H4L /// HIST2H4A /// HIST2H4B /// HIST4H4 | histone cluster 1, H4a /// histone cluster 1, H4b /// histone cluster 1, H4c /// histone cluster 1, H4d /// histone cluster 1, H4e /// histone cluster 1, H4f /// histone cluster 1, H4h /// histone cluster 1, H4i /// histone cluster 1, H4j /// histone cluster 1, H4k /// histone cluster 1, H4l /// histone cluster 2, H4a /// histone cluster 2, H4b /// histone cluster 4, H4 |
| 218355_at | 18259 | 0.00278 | KIF4A | kinesin family member 4A |
| 218883_s_at | 18786 | 0.00283 | MLF1IP | MLF1 interacting protein |
| 204267_x_at | 4333 | 0.00287 | PKMYT1 | protein kinase, membrane associated tyrosine/threonine 1 |
| 218662_s_at | 18565 | 0.00292 | NCAPG | non-SMC condensin I complex, subunit G |
| 202107_s_at | 2176 | 0.00296 | MCM2 | minichromosome maintenance complex component 2 |
| 205024_s_at | 5090 | 0.00301 | RAD51 | RAD51 homolog (S. cerevisiae) |
| 207165_at | 7230 | 0.00305 | HMMR | hyaluronan-mediated motility receptor (RHAMM) |
| 213011_s_at | 12933 | 0.0031 | TPI1 | triosephosphate isomerase 1 |
| 201710_at | 1779 | 0.00314 | MYBL2 | v-myb myeloblastosis viral oncogene homolog (avian)-like 2 |
| 218741_at | 18644 | 0.00319 | CENPM | centromere protein M |
| 202589_at | 2658 | 0.00323 | TYMS | thymidylate synthetase |
| 204825_at | 4891 | 0.00328 | MELK | maternal embryonic leucine zipper kinase |

Figure 25 - Continued

| | | | | |
|---|---|---|---|---|
| 205644_s_at | 5710 | 0.00332 | 0.0897276 | SNRPG | small nuclear ribonucleoprotein polypeptide G |
| 218115_at | 18019 | 0.00337 | 0.0907325 | ASF1B | ASF1 anti-silencing function 1 homolog B (S. cerevisiae) |
| 213007_at | 12929 | 0.00341 | 0.0907334 | FANCI | Fanconi anemia, complementation group I |
| 206102_at | 6167 | 0.00346 | 0.0909035 | GINS1 | GINS complex subunit 1 (Psf1 homolog) |
| 204170_s_at | 4236 | 0.0035 | 0.0909663 | CKS2 | CDC28 protein kinase regulatory subunit 2 |
| 209464_at | 9496 | 0.00355 | 0.0911092 | AURKB | aurora kinase B |
| 202094_at | 2163 | 0.00359 | 0.0914813 | BIRC5 | baculoviral IAP repeat containing 5 |
| 213088_s_at | 13010 | 0.00364 | 0.0916229 | DNAJC9 | DnaJ (Hsp40) homolog, subfamily C, member 9 |
| 211762_s_at | 11700 | 0.00368 | 0.0920088 | KPNA2 | karyopherin alpha 2 (RAG cohort 1, importin alpha 1) |
| 221521_s_at | 21423 | 0.00372 | 0.0920809 | GINS2 | GINS complex subunit 2 (Psf2 homolog) |
| 217938_s_at | 17842 | 0.00377 | 0.0921871 | KCMF1 | potassium channel modulatory factor 1 |
| 221677_s_at | 21577 | 0.00381 | 0.0924331 | DONSON | downstream neighbor of SON |
| 205436_s_at | 5502 | 0.00386 | 0.0927994 | H2AFX | H2A histone family, member X |
| 218755_at | 18658 | 0.0039 | 0.0929698 | KIF20A | kinesin family member 20A |
| 213911_s_at | 13829 | 0.00395 | 0.0929767 | H2AFZ | H2A histone family, member Z |
| 200822_x_at | 891 | 0.00399 | 0.0929927 | TPI1 | triosephosphate isomerase 1 |
| 213453_x_at | 13373 | 0.00404 | 0.0930206 | GAPDH | glyceraldehyde-3-phosphate dehydrogenase |
| 203276_at | 3342 | 0.00408 | 0.0931322 | LMNB1 | lamin B1 |
| 219787_s_at | 19690 | 0.00413 | 0.093322 | ECT2 | epithelial cell transforming sequence 2 oncogene |
| 212022_s_at | 11947 | 0.00417 | 0.0934029 | MKI67 | antigen identified by monoclonal antibody Ki-67 |
| 204244_s_at | 4310 | 0.00422 | 0.0934278 | DBF4 | DBF4 homolog (S. cerevisiae) |
| 200039_s_at | 601 | 0.00426 | 0.0935405 | PSMB2 | proteasome (prosome, macropain) subunit, beta type, 2 |
| 218447_at | 18351 | 0.00431 | 0.0935546 | CMC2 | COX assembly mitochondrial protein 2 homolog (S. cerevisiae) |
| 207183_at | 7247 | 0.00435 | 0.0935573 | GPR19 | G protein-coupled receptor 19 |
| 213226_at | 13147 | 0.0044 | 0.0936168 | CCNA2 | cyclin A2 |
| 221258_s_at | 21160 | 0.00444 | 0.0936256 | KIF18A | kinesin family member 18A |
| 218585_s_at | 18489 | 0.00449 | 0.0941146 | DTL | denticleless E3 ubiquitin protein ligase homolog (Drosophila) |

Figure 25 - Continued

| Probe Set ID | Gene Symbol | Gene Title | Entrez Gene ID | Cytoband |
|---|---|---|---|---|
| 200039_s_at | PSMB2 | proteasome (prosome, macropain) subunit, beta type, 2 | 5690 | 1p34.2 |
| 200822_x_at | TPI1 | triosephosphate isomerase 1 | 7167 | 12p13 |
| 201088_at | KPNA2 | karyopherin alpha 2 (RAG cohort 1, importin alpha 1) | 3838 | 17q24.2 |
| 201291_s_at | TOP2A | topoisomerase (DNA) II alpha 170kDa | 7153 | 17q21-q22 |
| 201292_at | TOP2A | topoisomerase (DNA) II alpha 170kDa | 7153 | 17q21-q22 |
| 201584_s_at | DDX39A | DEAD (Asp-Glu-Ala-Asp) box polypeptide 39A | 10212 | 19p13.12 |
| 201710_at | MYBL2 | v-myb myeloblastosis viral oncogene homolog (avian)-like 2 | 4605 | 20q13.1 |
| 201890_at | RRM2 | ribonucleotide reductase M2 | 6241 | 2p25-p24 |
| 201930_at | MCM6 | minichromosome maintenance complex component 6 | 4175 | 2q21 |
| 202094_at | BIRC5 | baculoviral IAP repeat containing 5 | 332 | 17q25 |
| 202095_s_at | BIRC5 | baculoviral IAP repeat containing 5 | 332 | 17q25 |
| 202107_s_at | MCM2 | minichromosome maintenance complex component 2 | 4171 | 3q21 |
| 202233_s_at | UQCRH /// UQCRHL | ubiquinol-cytochrome c reductase hinge protein /// ubiquinol-cytochrome c reductase hinge protein-like | 7388 /// 440567 | 1p34.1 /// 1p36.21 |
| 202503_s_at | KIAA0101 | KIAA0101 | 9768 | 15q22.31 |
| 202580_x_at | FOXM1 | forkhead box M1 | 2305 | 12p13 |
| 202589_at | TYMS | thymidylate synthetase | 7298 | 18p13.32 |
| 202705_at | CCNB2 | cyclin B2 | 9133 | 15q22.2 |
| 202779_s_at | UBE2S | ubiquitin-conjugating enzyme E2S | 27338 | 19q13.43 |
| 202870_s_at | CDC20 | cell division cycle 20 homolog (S. cerevisiae) | 991 | 1p34.1 |
| 202954_at | UBE2C | ubiquitin-conjugating enzyme E2C | 11065 | 20q13.12 |
| 203022_at | RNASEH2A | ribonuclease H2, subunit A | 10535 | 19p13.2 |
| 203046_s_at | TIMELESS | timeless homolog (Drosophila) | 8914 | 12q13.3 |
| 203213_at | CDK1 | cyclin-dependent kinase 1 | 983 | 10q21.1 |
| 203214_x_at | CDK1 | cyclin-dependent kinase 1 | 983 | 10q21.1 |
| 203276_at | LMNB1 | lamin B1 | 4001 | 5q23.2 |
| 203362_s_at | MAD2L1 | MAD2 mitotic arrest deficient-like 1 (yeast) | 4085 | 4q27 |
| 203432_at | TMPO | thymopoietin | 7112 | 12q22 |
| 203554_x_at | PTTG1 | pituitary tumor-transforming 1 | 9232 | 5q33.1 |
| 203755_at | BUB1B | budding uninhibited by benzimidazoles 1 homolog beta (yeast) | 701 | 15q15 |
| 203764_at | DLGAP5 | discs, large (Drosophila) homolog-associated protein 5 | 9787 | 14q22.3 |
| 204026_s_at | ZWINT | ZW10 interactor | 11130 | 10q21-q22 |
| 204033_at | TRIP13 | thyroid hormone receptor interactor 13 | 9319 | 5p15.33 |
| 204092_s_at | AURKA | aurora kinase A | 6790 | 20q13 |
| 204146_at | RAD51AP1 | RAD51 associated protein 1 | 10635 | 12p13.2-p13.1 |
| 204162_at | NDC80 | NDC80 kinetochore complex component homolog (S. cerevisiae) | 10403 | 18p11.32 |
| 204170_s_at | CKS2 | CDC28 protein kinase regulatory subunit 2 | 1164 | 9q22 |
| 204244_s_at | DBF4 | DBF4 homolog (S. cerevisiae) | 10926 | 7q21.3 |
| 204267_x_at | PKMYT1 | protein kinase, membrane associated tyrosine/threonine 1 | 9088 | 16p13.3 |
| 204444_at | KIF11 | kinesin family member 11 | 3832 | 10q24.1 |
| 204641_at | NEK2 | NIMA (never in mitosis gene a)-related kinase 2 | 4751 | 1q32.2-q41 |
| 204817_at | ESPL1 | extra spindle pole bodies homolog 1 (S. cerevisiae) | 9700 | 12q |
| 204822_at | TTK | TTK protein kinase | 7272 | 6q13-q21 |
| 204825_at | MELK | maternal embryonic leucine zipper kinase | 9833 | 9p13.2 |

Figure 26

| | | | | |
|---|---|---|---|---|
| 204962_s_at | C2orf18 /// CENPA | chromosome 2 open reading frame 18 /// centromere protein A | 1058 /// 54978 | 2p23.3 /// 3p24-p21 |
| 205024_s_at | RAD51 | RAD51 homolog (S. cerevisiae) | 5888 | 15q15.1 |
| 205034_at | CCNE2 | cyclin E2 | 9134 | 8q22.1 |
| 205046_at | CENPE | centromere protein E, 312kDa | 1062 | 4q24-q25 |
| 205436_s_at | H2AFX | H2A histone family, member X | 3014 | 11q23.3 |
| 205644_s_at | SNRPG | small nuclear ribonucleoprotein polypeptide G | 6637 | 2p13.3 |
| | HIST1H3A /// HIST1H4B /// HIST1H4C /// HIST1H4D /// HIST1H4E /// HIST1H4F /// HIST1H4H /// HIST1H4I /// HIST1H4J /// HIST1H4K /// HIST1H4L /// HIST2H4A /// HIST2H4B | histone cluster 1, H4a /// histone cluster 1, H4b /// histone cluster 1, H4c /// histone cluster 1, H4d /// histone cluster 1, H4e /// histone cluster 1, H4f /// histone cluster 1, H4h /// histone cluster 1, H4i /// histone cluster 1, H4j /// histone cluster 1, H4k /// histone cluster 2, H4a /// histone cluster 2, H4 | 121504 /// 554313 /// 8294 /// 8359 /// 8360 /// 8361 /// 8362 /// 8363 /// 8364 /// 8365 /// 8366 /// 8367 /// 8368 /// 8370 | 12p12.3 /// 1q21 /// 1q21.2 /// 6p21.33 /// 6p22.1 |
| 205967_at | GINS1 | GINS complex subunit 1 (Psf1 homolog) | 9837 | 20p11.21 |
| 206102_at | KIF14 | kinesin family member 14 | 9928 | 1q32.1 |
| 206364_at | HMMR | hyaluronan-mediated motility receptor (RHAMM) | 3161 | 5q33.2-qter |
| 207155_at | GPR19 | G protein-coupled receptor 19 | 2842 | 12p12.3 |
| 207183_at | CENPF | centromere protein F, 350/400kDa (mitosin) | 1063 | 1q32-q41 |
| 207828_s_at | AURKA | aurora kinase A | 6790 | 20q13 |
| 208079_s_at | KIF2C | kinesin family member 2C | 11004 | 1p34.1 |
| 209464_at | AURKB | aurora kinase B | 9212 | 17p13.1 |
| 209642_at | BUB1 | budding uninhibited by benzimidazoles 1 homolog (yeast) | 699 | 2q14 |
| 209680_s_at | KIFC1 | kinesin family member C1 | 3833 | 6p21.3 |
| 209714_s_at | CDKN3 | cyclin-dependent kinase inhibitor 3 | 1033 | 14q22 |
| 209773_s_at | RRM2 | ribonucleotide reductase M2 | 6241 | 2p25-p24 |
| 210052_s_at | TPX2 | TPX2, microtubule-associated, homolog (Xenopus laevis) | 22974 | 20q11.2 |
| 210559_s_at | CDK1 | cyclin-dependent kinase 1 | 983 | 10q21.1 |
| 211762_s_at | KPNA2 | karyopherin alpha 2 (RAG cohort 1, importer alpha 1) | 3838 | 17q24.2 |
| 212022_s_at | MKI67 | antigen identified by monoclonal antibody Ki-67 | 4288 | 10q26.2 |
| 212949_at | NCAPH | non-SMC condensin I complex, subunit H | 23397 | 2q11.2 |
| 213007_at | FANCI | Fanconi anemia, complementation group I | 55215 | 15q26.1 |
| 213008_at | FANCI | Fanconi anemia, complementation group I | 55215 | 15q26.1 |
| 213011_s_at | TPI1 | triosephosphate isomerase 1 | 7167 | 12p13 |
| 213088_s_at | DNAJC9 | DnaJ (Hsp40) homolog, subfamily C, member 9 | 23234 | 10q22.2 |
| 213226_at | CCNA2 | cyclin A2 | 890 | 4q25-q31 |
| 213453_x_at | GAPDH | glyceraldehyde-3-phosphate dehydrogenase | 2597 | 12p13 |
| 213931_s_at | H2AFZ | H2A histone family, member Z | 3015 | 4q24 |
| 214710_s_at | CCNB1 | cyclin B1 | 891 | 5q12 |
| 217938_s_at | KCMF1 | potassium channel modulatory factor 1 | 56888 | 2p11.2 |
| 218039_at | PRC1 | protein regulator of cytokinesis 1 | 9055 | 15q26.1 |
| 218115_at | NUSAP1 | nucleolar and spindle associated protein 1 | 51203 | 15q15.1 |
| 218308_at | ASF1B | ASF1 anti-silencing function 1 homolog B (S. cerevisiae) | 55723 | 19p13.12 |
| 218355_at | TACC3 | transforming, acidic coiled-coil containing protein 3 | 10460 | 4p16.3 |
| | KIF4A | kinesin family member 4A | 24137 | Xq13.1 |

Figure 26 - Continued

| | | | | |
|---|---|---|---|---|
| 218847_at | CMC2 | COX assembly mitochondrial protein 2 homolog (S. cerevisiae) | 56942 | 16q23.2 |
| 218542_at | CEP55 | centrosomal protein 55kDa | 55165 | 10q23.33 |
| 218585_s_at | DTL | denticleless E3 ubiquitin protein ligase homolog (Drosophila) | 51514 | 1q32 |
| 218662_s_at | NCAPG | non-SMC condensin I complex, subunit G | 64151 | 4p15.33 |
| 218726_at | HJURP | Holliday junction recognition protein | 55355 | 2q37.1 |
| 218741_at | CENPM | centromere protein M | 79019 | 22q13.2 |
| 218755_at | KIF20A | kinesin family member 20A | 10112 | 5q31 |
| 218883_s_at | MLF1IP | MLF1 interacting protein | 79682 | 4q35.1 |
| 219787_s_at | ECT2 | epithelial cell transforming sequence 2 oncogene | 1894 | 3q26.1-q26.2 |
| 219918_s_at | ASPM | asp (abnormal spindle) homolog, microcephaly associated (Drosophila) | 259266 | 1q31 |
| 220651_s_at | MCM10 | minichromosome maintenance complex component 10 | 55388 | 10p13 |
| 221258_s_at | KIF18A | kinesin family member 18A | 81930 | 11p14.1 |
| 221436_s_at | CDCA3 | cell division cycle associated 3 | 83461 | 12p13 |
| 221520_s_at | CDCA8 | cell division cycle associated 8 | 55143 | 1p34.3 |
| 221521_s_at | GINS2 | GINS complex subunit 2 (Psf2 homolog) | 51659 | 16q24.1 |
| 221677_s_at | DONSON | downstream neighbor of SON | 29980 | 21q22.1 |
| 222039_at | KIF18B | kinesin family member 18B | 146909 | 17q21.31 |
| 222077_s_at | RACGAP1 | Rac GTPase activating protein 1 | 29127 | 12q13.12 |
| 38158_at | ESPL1 | extra spindle pole bodies homolog 1 (S. cerevisiae) | 9700 | 12q |
| 203033_s_at | PSMB2 | proteasome (prosome, macropain) subunit, beta type, 2 | 5690 | 1p34.2 |

Figure 26 - Continued

BIOMARKER SPAG5

This application is a continuation of U.S. National application Ser. No. 14/404,163, filed Nov. 26, 2014, which is a U.S. national stage under 35 U.S.C. § 371 of International Patent Application No. PCT/GB2013/051465, filed May 31, 2013, which claims priority to Great Britain Patent Application No. 1209802.6, filed Jun. 1, 2012, each of which is hereby incorporated by reference in its entirety.

This invention relates to a method of determining the prognosis and suitable treatment of cancer in a subject by measuring the level of expression of SPAG5. In particular, it relates to a method where high expression of SPAG5 in tumour cells correlates with aggressive tumours.

SPAG5 has been found to be involved in the functional and dynamic regulation of mitotic spindles, and to be essential for progression through mitosis and chromosome segregation fidelity. Although defects in chromosomal segregation contribute to chromosome instability and aneuploidy, a hallmark of malignant cells, it could be the cancer cell's ultimate vulnerability. Drugs that interfere with the normal progression of mitosis belong to the most successful chemotherapeutic compounds currently used for anti-cancer treatment. Classically, these drugs are represented by microtubule binding drugs that inhibit the function of the mitotic spindle in order to halt the cell cycle in mitosis and to induce apoptosis in tumour cells. However, since microtubule inhibitors not only target proliferating cells severe side effects limit their use. Therefore, there is a particular interest in developing novel" next generation" anti-mitotic drugs that target non-microtubule structures. In addition, approaches of cell cycle checkpoint abrogation during mitosis and at the G2/M transition inducing mitosis-associated tumour cell death are promising new strategies for anticancer therapy.

There has been a recent shift in cancer therapy from 'one size fits all' to a personalized and tailored treatment for individual patients to increase efficiency and avoid unnecessary toxicity. There is an urgent need to identify biomarkers that can help in risk assessments and could act as novel therapeutic targets. Many different cancers are amenable to personalised and tailored treatment for individual patents. Biomarkers can be used to predict the prognosis for a particular patient and to identify treatments that are more likely to work on cancers with particular biomarkers. Cancers may be classified by biomarkers instead or as well as by the tissue of origin. Breast and ovarian cancers remain the most common cancers and is the leading cause of cancer deaths in women. In spite of improved outcome by earlier detection, and recent advances in adjuvant therapy (AT), many patients still develop recurrence.

Tumour biology directed personalized risk assessment stratification may inform effective treatment options to improve patient outcomes in early stage disease. Tumour markers can be used to assess the aggressiveness of a particular tumour and the likelihood of a particular tumour to recur or metastasise. Hence, biomarkers can help to plan treatment that is individualised to the particular patient and biology of a particular tumour.

Tumours are graded as an indication of their likelihood of spreading or recurring. Small tumours that are found at an early stage may be considered to have a low risk of spreading (metastasising) or recurring. Tumours considered to be of higher risk of spreading or recurring may be treated more aggressively, often by using adjuvant therapy, for example, chemotherapy, to target any possible remaining cancer cells, after removal of the main tumour. The assessment of the risk of a tumour spreading is currently difficult. Some tumours considered to be low risk, nevertheless spread or recur. On the other hand, adjuvant therapies themselves carry risks and causes side effects and therefore they are preferably used only where necessary.

It is an aim of the present invention to provide a biomarker that may be used to give an indication of the prognosis of cancer in an individual and/or which may also be used to assess the type of treatment that is appropriate for a particular tumour or individual.

In a first aspect the present invention provides a method for obtaining an indication useful in determining the appropriate treatment for a subject comprising the steps of:
  i. determining the expression level of SPAG5 in a tumour tissue sample from said subject; and
  ii. comparing the expression level of SPAG5 determined in step (i) with one or more reference values.

When evaluating the appropriate treatment for a subject who has a cancer it is valuable to obtain indications about the tumour such as the likelihood that it has already spread, the likelihood of it spreading in the future, how aggressive that particular tumour is and which chemotherapeutic agents that particular tumour is likely to be sensitive to.

These indications may help a clinician to determine the appropriate treatment for the subject.

The sample may be a sample of tumour tissue. The sample may be any sample of tumour tissue that comprises cancer cells. The sample may be a cell or a number of cells. In one embodiment the sample may be a core from the centre or the periphery of a tumour.

High expression of SPAG5 may indicate that the tumour is likely to be sensitive to a platinum chemotherapy agent or an anthracycline or combination chemotherapy with CMF (cyclophosphamide, methotrexate and fluorouracil 5FU).

Low expression of SPAG5 may indicate that the tumour is likely to be resistant to a platinum chemotherapy agent or an anthracycline or combination chemotherapy with CMF (cyclophosphamide, methotrexate and fluorouracil 5FU).

High expression of SPAG5 may indicate that the tumour is likely to be sensitive to a combination of an anthracycline and HERCEPTIN® (trastuzumab, anti-HER2 monoclonal antibody).

High expression of SPAG5 may indicate that the tumour is likely to be sensitive to a platinum chemotherapy agent. If the tumour is sensitive to a chemotherapy agent the tumour cells may be killed by the chemotherapy agent. High expression of SPAG5 may indicate that the tumour is not platinum resistant. Any type of tumour that has a high level of expression of SPAG5 may be sensitive to a platinum chemotherapy agent, the cancer may any cancer that is treatable by a platinum chemotherapy agent and/or any cancer that is treatable by an anthracycline, for example, the cancer may be breast cancer, ovarian cancer, gastric cancer, pancreatic cancer, prostate cancer, head and neck cancers, lung cancer or colorectal cancer.

Low expression of SPAG5 may indicate that the tumour is likely to be resistant to a platinum chemotherapy agent. Platinum resistant tumours may be defined as tumours which progress during first-line platinum chemotherapy or relapse within 6 months after treatment with a platinum chemotherapy agent.

A platinum chemotherapy agent may, for example, be cisplatin, carboplatin or oxaliplatin.

High levels of SPAG5 expression may indicate that a tumour is likely to be sensitive to an anthracycline. An anthracycline may, for example, be Daunorubicin (Daunomycin), Daunorubicin (liposomal), Doxorubicin (Adriamycin), Doxorubicin (liposomal), Epirubicin, Idarubicin, Valrubicin or Mitoxantrone.

High levels of SPAG5 expression may indicate that the tumour is likely to be sensitive to a combination of an anthracycline and HERCEPTIN® (trastuzumab, anti-HER2 monoclonal antibody). Any type of tumour that has high levels of SPAG5 expression may be sensitive to synthetic lethality, the cancer may, for example, be breast cancer, ovarian cancer, gastric cancer, pancreatic cancer or colorectal cancer.

High expression of SPAG5 may indicate that the tumour may have an aggressive phenotype and is more likely to metastasise.

The expression level of SPAG5 may be determined, for example, by evaluating histological staining or by evaluating mRNA levels.

Sections of the tumour may be stained, for example with a labelled antibody against SPAG5, levels of SPAG5 staining may be evaluated semi-quantitatively and given a score for the amount of staining. The amount of staining may be compared to a suitable reference value. The reference value may be the amount of staining in normal tissue, for example, the staining in a breast cancer tumour sample may be compared to staining in normal breast tissue. This may be obtained from a sample of non-diseased tissue taken from the same subject or from a different subject.

The amount of staining may be compared to standard histological standards. Methods for assessing the amount of expression by histological staining are known in the art. In one method the staining is rated as 0=no staining, 1=weak staining, 2=moderate staining, 3=strong staining. A staining level of 0 or 1 would be considered to indicate low or negative SPAG5 expression. A staining level of 2 or 3 may be considered to indicate high SPAG5 expression. In addition, the percentage of the whole section that is stained may be estimated between 0% and 100%. The intensity of staining and the percentage staining may be multiplied together to provide a HEAD score (also called histochemical score or H-score).

A HEAD score of less than or equal to 100 may indicate low or negative expression of SPAG5. A HEAD score of greater than 100 may indicate high expression of SPAG5. Normal, non-cancerous breast cells may have high SPAG5 expression.

The reference value against which the level of expression is evaluated may be the level of expression in normal tissues or may be standard histo-pathological criteria. The level of expression of SPAG5 in a tumour cell or tissue sample may be evaluated by measuring the presence or amount of mRNA encoding SPAG5. The level of expression of SPAG5 in a tumour cell or tissue sample may be evaluated by other standard quantitative or semi-quantitative techniques.

Where the tumour sample has high SPAG5 expression level this may be significantly associated with poor prognosis for the subject.

Poor prognosis may be defined as a 2 fold higher risk of death from cancer, cancer recurrence or distant metastasis within 10 years compared to a cancer with low SPAG5 expression.

The method of the invention may include a first step of determining a subject has breast cancer by other means.

Tumours with high levels of SPAG5 expression, (also called SPAG5+ tumours) may be biologically more aggressive. In breast cancer this may be evidenced by high histological grade, pleomorphism, glandular de-differentiation, absence of hormonal receptors, and presence of basal like phenotypes and triple negative phenotypes. Triple-negative breast cancer refers to any breast cancer that does not express the genes for estrogen receptor (ER), progesterone receptor (PR) or Her2/neu.

High levels of expression of SPAG5 is an indicator of poor prognosis that is independent of the finding of a triple negative phenotype. Therefore, classification of a tumour by SPAG5 expression level provides additional information that may be useful in a more detailed classification providing better guidance for treatment and better estimates for prognosis.

The expression of SPAG5 may be evaluated by any suitable method. For example if protein levels are to be determined any of the group comprising immunoassays, spectrometry, western blot, ELISA, immunoprecipitation, slot or dot blot assay, isoelectric focussing, SDS-PAGE and antibody microarray immunohistological staining, radio immunoassay (RIA), fluoroimmunoassay, an immunoassay using an avidin-biotin or streptoavidin-biotin system, etc and combinations thereof may be used. These methods are well known to persons skilled in the art. Other methods may also be used.

The expression of SPAG5 may be evaluated qualitatively, for example, a sample may be assessed as positive or negative for SPAG5 protein expression. This may for example be done using immunostaining of cells, using an antibody that binds SPAG5 protein. Cells, or tissue samples that are stained using an anti-SPAG5 antibody may be considered to express SPAG5 protein and cells or tissue samples that are not stained may be assessed as not expressing SPAG5 protein.

The expression level of SPAG5 in cells is evaluated quantitatively by quantifying the amount of SPAG5 protein or mRNA in tumour cells.

The methods of the present invention may be used to offer personalised medicine solutions. High SPAG5 expression may indicate a tumour phenotype that is likely to be more aggressive and more likely to spread or metastasise. Therefore, high SPAG5 expression in a tumour sample may indicate that it would be beneficial to use one or more adjuvant therapies to target cells that may remain after mastectomy or local excision of a tumour. The adjuvant therapy may be administered locally, systemically or both.

High SPAG5 expression in a tumour may indicate that the tumour should be treated as a high-risk tumour even if other indicators suggest it is a low-risk tumour.

Tumours may be categorised as high risk tumours or low risk tumours using a number of criteria and the type of treatment offered to the patient may depend on whether the tumour is considered low risk or high risk.

One well used method to classify breast cancer is the St. Gallen International Consensus Panel, this classifies low-risk breast cancer as having all of the following criteria: the cancer has not spread to the lymph nodes; the tumor is <2 cm in greatest dimension; the nuclei are small, with little increase or variation in size compared with breast epithelial cell nuclei, regular outlines, uniformity of nuclear chromatin; no cancer cells have invaded the blood or lymphatic vessels and cancer does not use the HER2/neu pathway to grow. This can be a complicated, time consuming and costly process.

Another method for assessing whether a tumour is high or low risk is the Nottingham Prognostic Index (NPI).

Patients with breast cancer may be treated by removing the breast tumour by surgery (mastectomy or wide local excision), this may be followed by radiotherapy. Adjuvant therapy may be used based on prognostic and predictive factor status, including NPI, oestrogen receptor-a (ER-a) status, and menopausal status. Patients with NPI scores of <3.4 (low risk) may or may not be given adjuvant therapy. In pre-menopausal patients with NPI scores of ≥3.4 (high risk), adjuvant therapy is usually given, for example, classical Cyclophosphamide, Methotrexate, and 5-Flourouracil (CMF) chemotherapy may be given; patients with ER-a positive tumours may also be offered hormone therapy. Postmenopausal patients with NPI scores of ≥3.4 and ER-a positivity may also be offered hormone therapy, while ER-a negative patients received classical CMF chemotherapy.

Adjuvant therapy is treatment that is given in addition to the primary, main or initial treatment, for example mastectomy or local excision of a tumour. An example of adjuvant therapy is the additional treatment usually given after surgery where all detectable disease has been removed, but where there remains a statistical risk of relapse due to occult disease.

In breast cancer, adjuvant therapy may comprise a systemic adjuvant therapy such as chemotherapy, for example using one or more of doxorubicin, HERCEPTIN® (trastuzumab, anti-HER2 monoclonal antibody), paclitaxel, docetaxel, cyclophosphamide, fluorouracil, and methotrexate. Another systemic adjuvant therapy may be hormonal therapy (HT), for example using tamoxifen or femara. Adjuvant therapy in breast cancer may be used in stage one and two breast cancer following lumpectomy, and in stage three breast cancer due to lymph node involvement.

Radiotherapy, especially after lumpectomy may also be considered an adjuvant therapy because it aims to treat a risk of the cancer recurring after the tumour has been removed. Radiotherapy is a local adjuvant therapy rather than a systemic adjuvant therapy.

For example, radiotherapy or systemic therapy is commonly given as adjuvant treatment after surgery for breast cancer. Systemic therapy consists of chemotherapy, immunotherapy or biological response modifiers or hormone therapy.

The method of the present invention may be carried out in vitro.

The subject may be a human. In another embodiment the subject may be a mammal, for example, a dog, cat, horse, cow, monkey, ape, rodent, hamster, rat, or guinea pig.

In another aspect the present invention provides the use of SPAG5 expression in a tumour tissue sample as a biomarker to determine prognosis of cancer in a subject.

High expression of SPAG5 may correlate with poor prognosis.

The invention provides a use of the determination of the expression level of SPAG5 in a tumour cell or tumour tissue sample as a means of assessing whether the tumour is sensitive to a compound or combination of compounds. The compound may be any chemotherapy agent. The compound may be a platinum chemotherapy agent or an anthracycline chemotherapy agent or a platinum chemotherapy agent in combination with HERCEPTIN® (trastuzumab, anti-HER2 monoclonal antibody).

In one aspect the present invention provides a kit for use in obtaining an indication useful in determining the most appropriate treatment for a subject, wherein the kit comprises at least one agent for determining the expression level of SPAG5 in a tumour tissue sample provided from the subject.

The agent may be an antibody or a labelled antibody that binds to SPAG5 protein.

The kit may further comprise instructions for suitable operational parameters in the form of a label or separate insert.

The kit may further comprise one or more SPAG5 protein samples to be used as standard(s) for calibration and comparison.

The present invention provides a method for identifying a compound useful in the treatment of cancer, wherein the method comprises the step of testing whether a compound binds to SPAG5, or is a modulator of SPAG5 activity, or is an inhibitor of SPAG5 activity or is an agonist of SPAG5 activity.

A compound that binds to SPAG5 or is a modulator of SPAG5 activity or is an inhibitor of SPAG5 activity or is an agonist of SPAG5 activity may affect the cell cycle, in particular it may affect cell division. A compound that modulates that activity of SPAG5. A compound identified by this method may be used in the treatment of cancer. The invention also provides use of a compound identified by this method in the treatment of cancer.

The present invention provides a modulator of SPAG5 activity for use in the treatment of cancer. The modulator may be an antibody that specifically binds to SPAG5. The modulator may be a monoclonal antibody that specifically binds to SPAG5. The modulator may be an agonist of SPAG5 activity or the modulator may be an antagonist of SPAG5 activity.

The modulator may be used in the treatment of a tumour that has increased SPAG5 expression.

The skilled man will appreciate that preferred features of any one embodiment and/or aspect of the invention may be applied to all other embodiments and/or aspects of the invention.

There now follows by way of example only a detailed description of the present invention with reference to the accompanying drawings, in which;

FIG. 1: Shows the results of an artificial neural network and pathway analysis which revealed that SPAG5 is one of the main hubs in KIF2C pathways and that SPAG5 expression is strongly correlated to expression of genes that are involved in mitotic cell cycle regulation especially anaphase phase and cell division, DNA repair and metastases.

Figure 2:
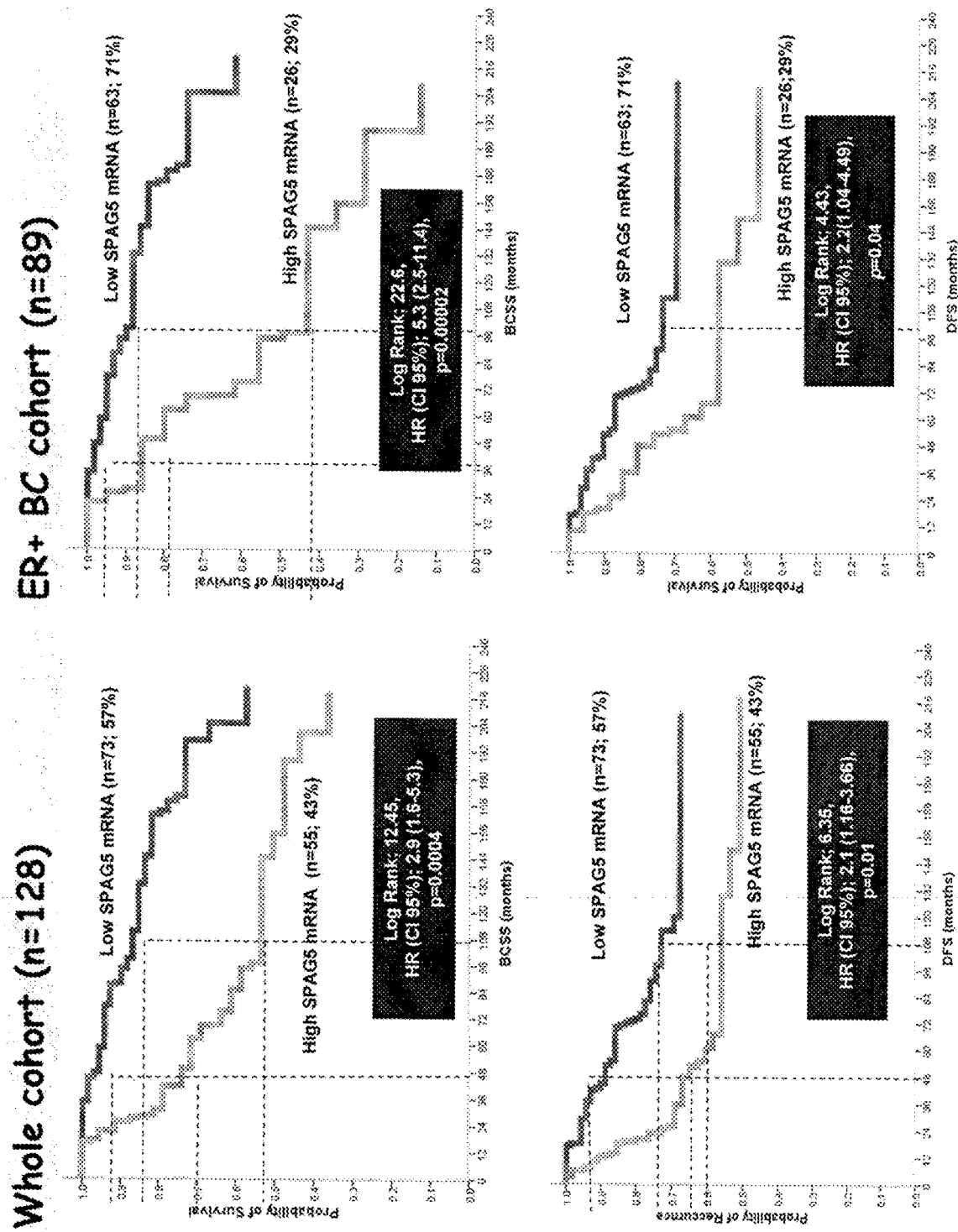

FIG. 2: Shows Kaplan Meier curves showing breast cancer specific survival (BCSS) and disease free survival (DFS) of patients with breast tumours that had low or high expression of SPAG5 mRNA. Left hand panels show survival of the whole cohort of 128 breast cancer patents. Right hand panels show survival of a sub-group with ER+ tumours.

FIG. 3: Shows a multivariate logistic regression model for SPAG5 RNA expression.

Figure 4:
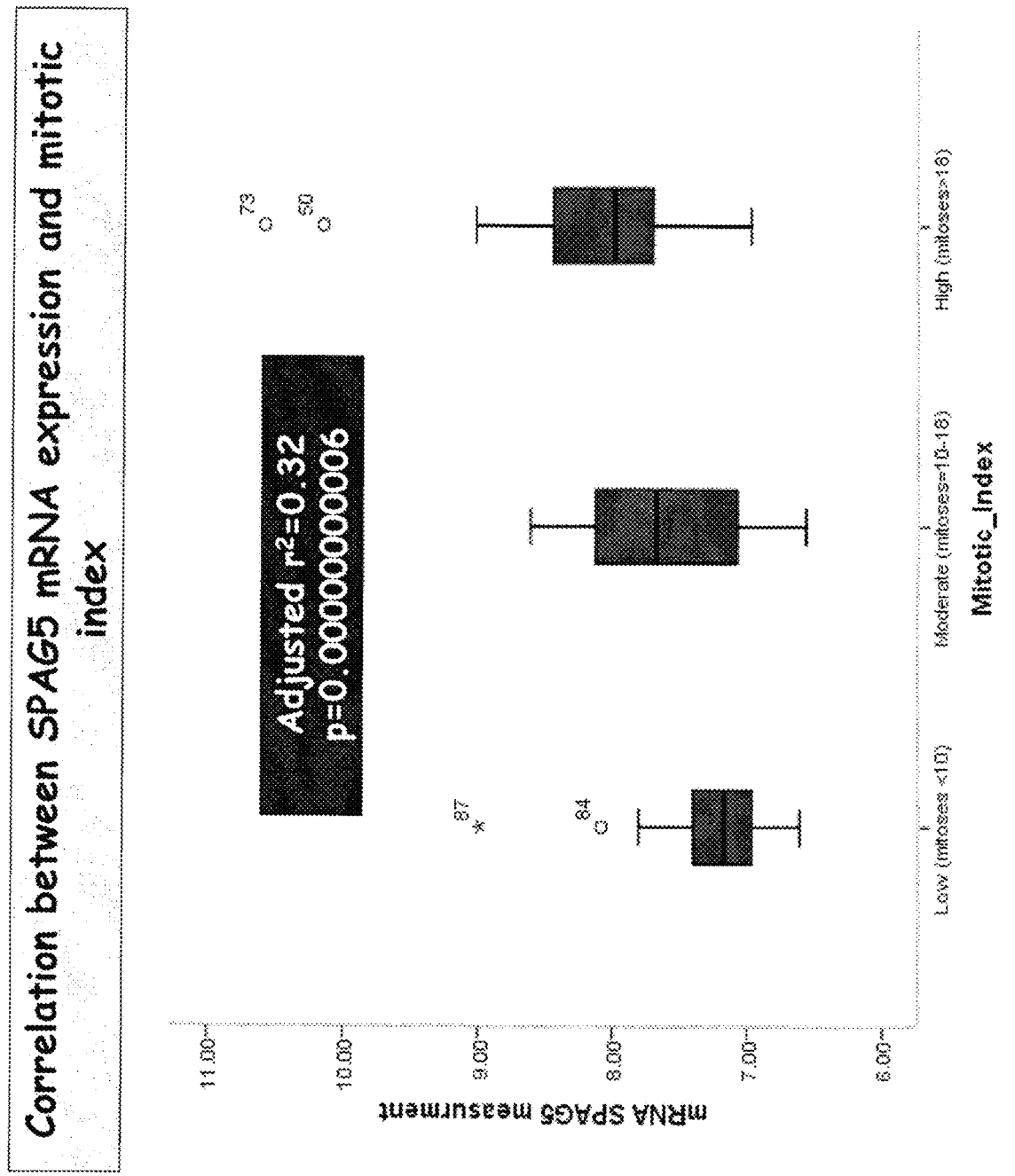

FIG. 4: Shows Dual immunoflurescent (IF) staining of SPAG5 (green) and proliferating cell nuclear antigen (PCNA, red) in breast cancer cell lines. Co-expression of SPAG5 and PCNA was expressed in 4 out of 5 of the breast cancer cell lines screened (MCF7, T47D, MDA468 and MDA231). In these breast cancer cells the IF staining strongly suggests that in proliferating cells (evidenced by PCNA staining) there are both co-expression of SPAG5 and PCNA as well as increased levels of expression of SPAG5 providing evidence for the importance of SPAG5 in cell proliferation. Furthermore there is evidence of localisation of SPAG5 within the centrosomes and spindles of dividing cells. In SkBr3 cells both SPAG5 and PCNA were expressed by the cells but there appeared to be no direct correlation between levels of SPAG5 and the proliferation of the cells.

Figure 5:
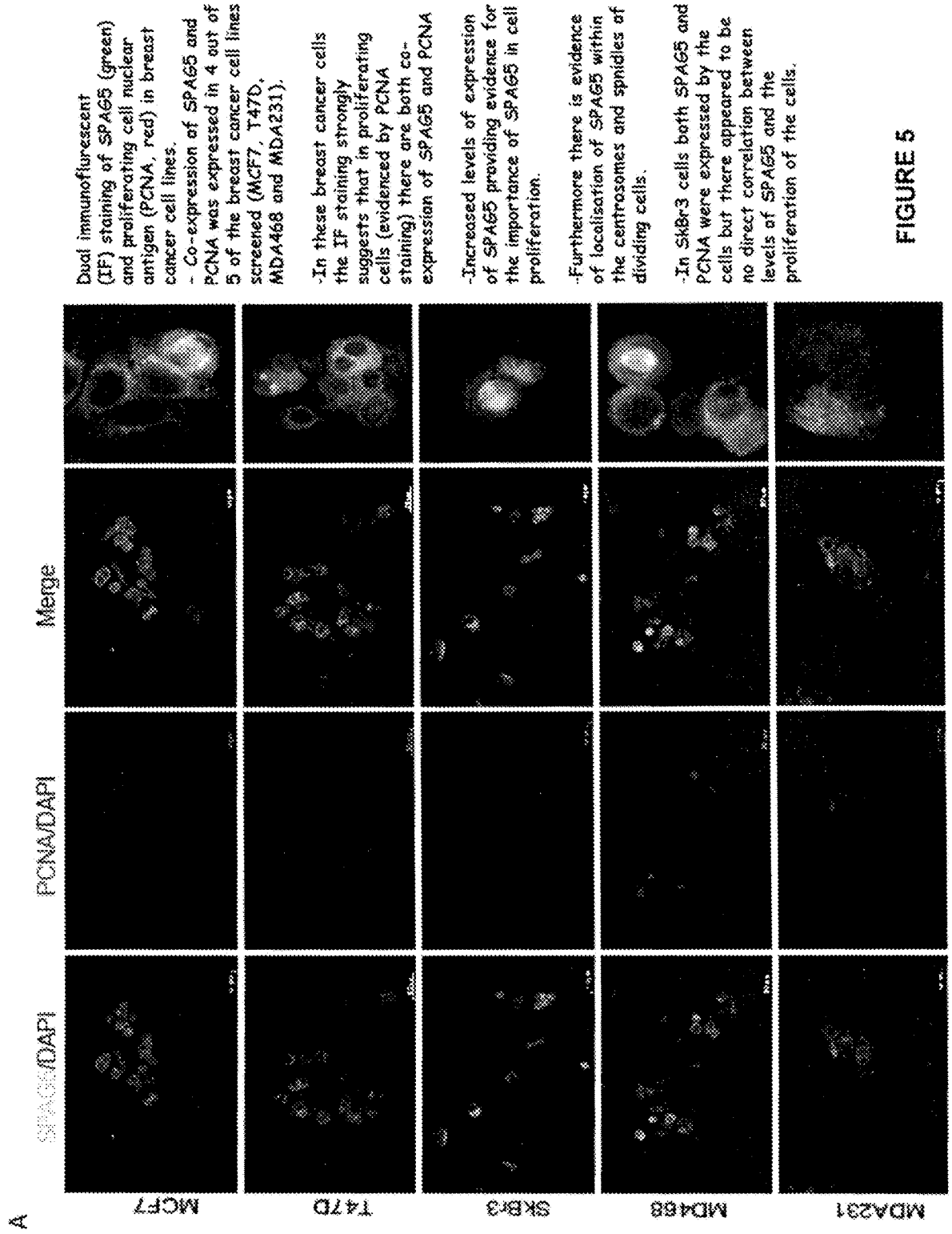

FIG. 5: Shows a correlation between SPAG5 mRNA expression and mitotic index.

Figure 6:
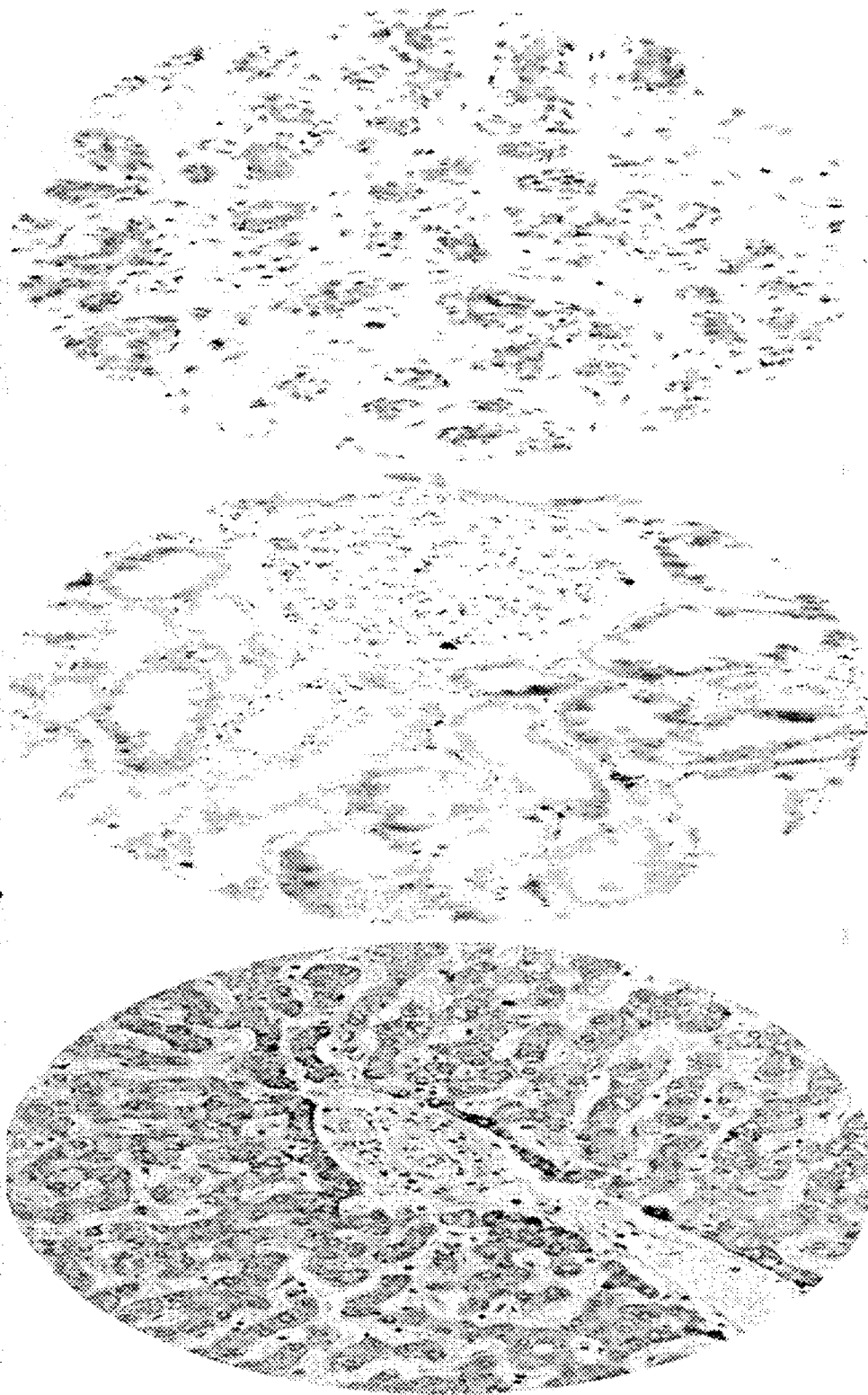

FIG. 6: Shows immunostained sections of normal tissue showing SPAG5 expression in normal, liver, kidney and breast tissue.

Figure 7:
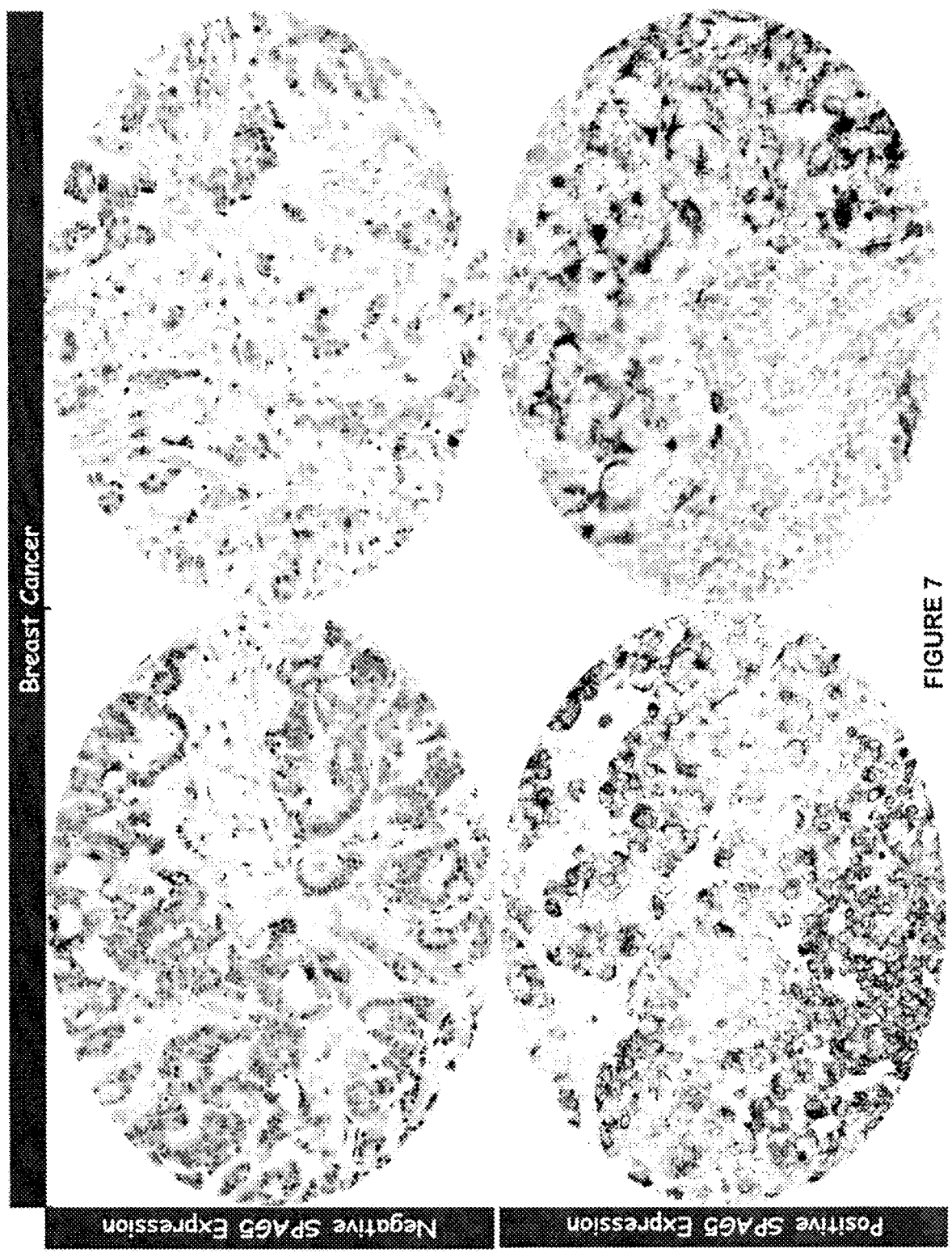

FIG. 7: Shows immunostained sections of breast cancer tissue with negative and with positive SPAG5 expression.

Figure 8:

FIG. 8: Shows immunostained sections of ovarian cancer tissue with either negative or positive SPAG5 expression (left hand panels) and immunostained sections of pancreatic cancer tissue with either negative or positive SPAG5 expression (right hand panels).

Figure 9:

FIG. 9: Shows immunostained sections of gastric cancer tissue with either negative or positive SPAG5 expression (left hand panels) and immunostained sections of colorectal cancer tissue with either negative or positive SPAG5 expression (right hand panels).

FIG. 10: Shows a multivariate logistic regression model for SPAG5 protein expression.

Figure 11:
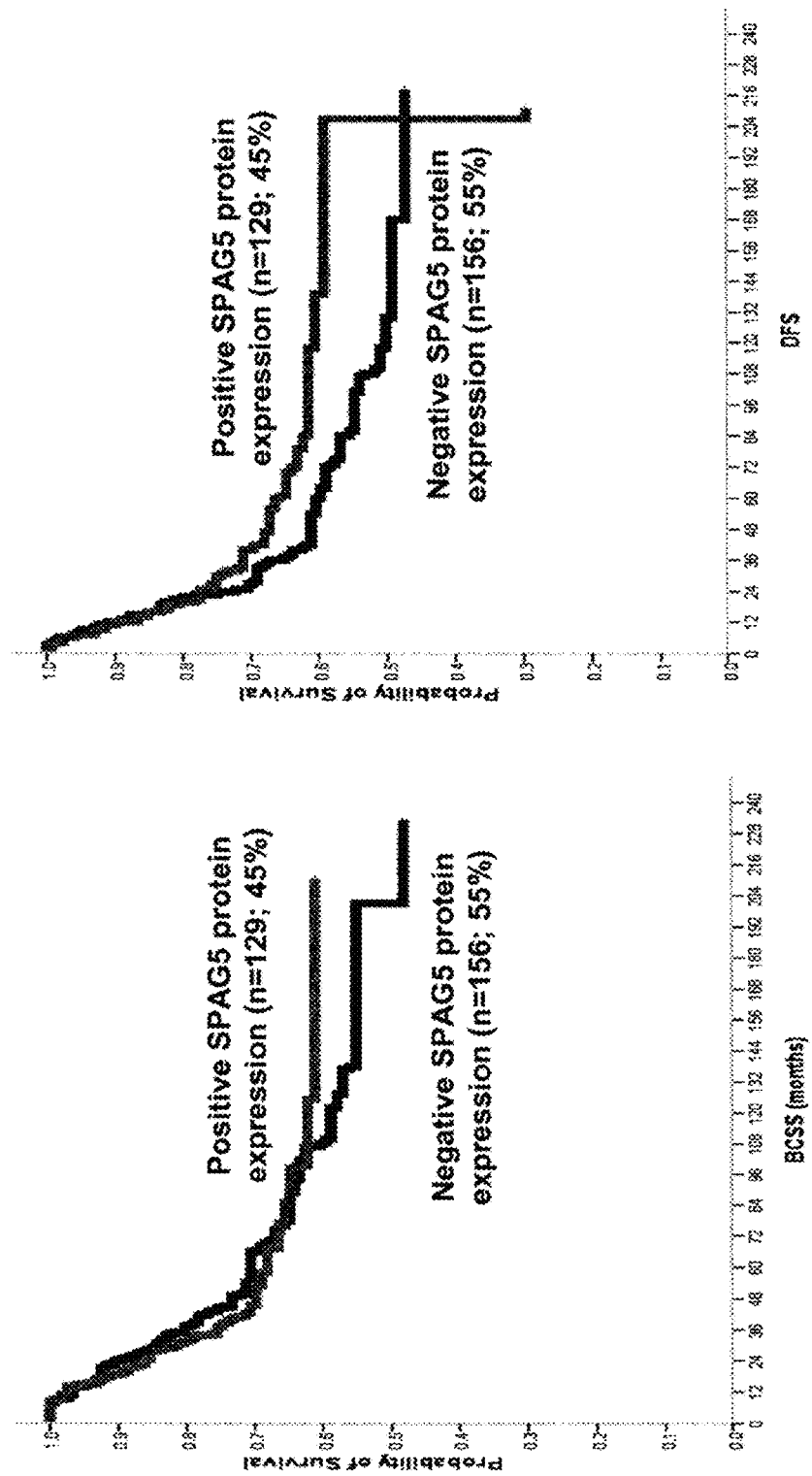

FIG. 11: Shows clinical outcome of high risk ER– Breast cancer patients who received either no adjuvant chemotherapy or received CMF (n=285).

Figure 12:
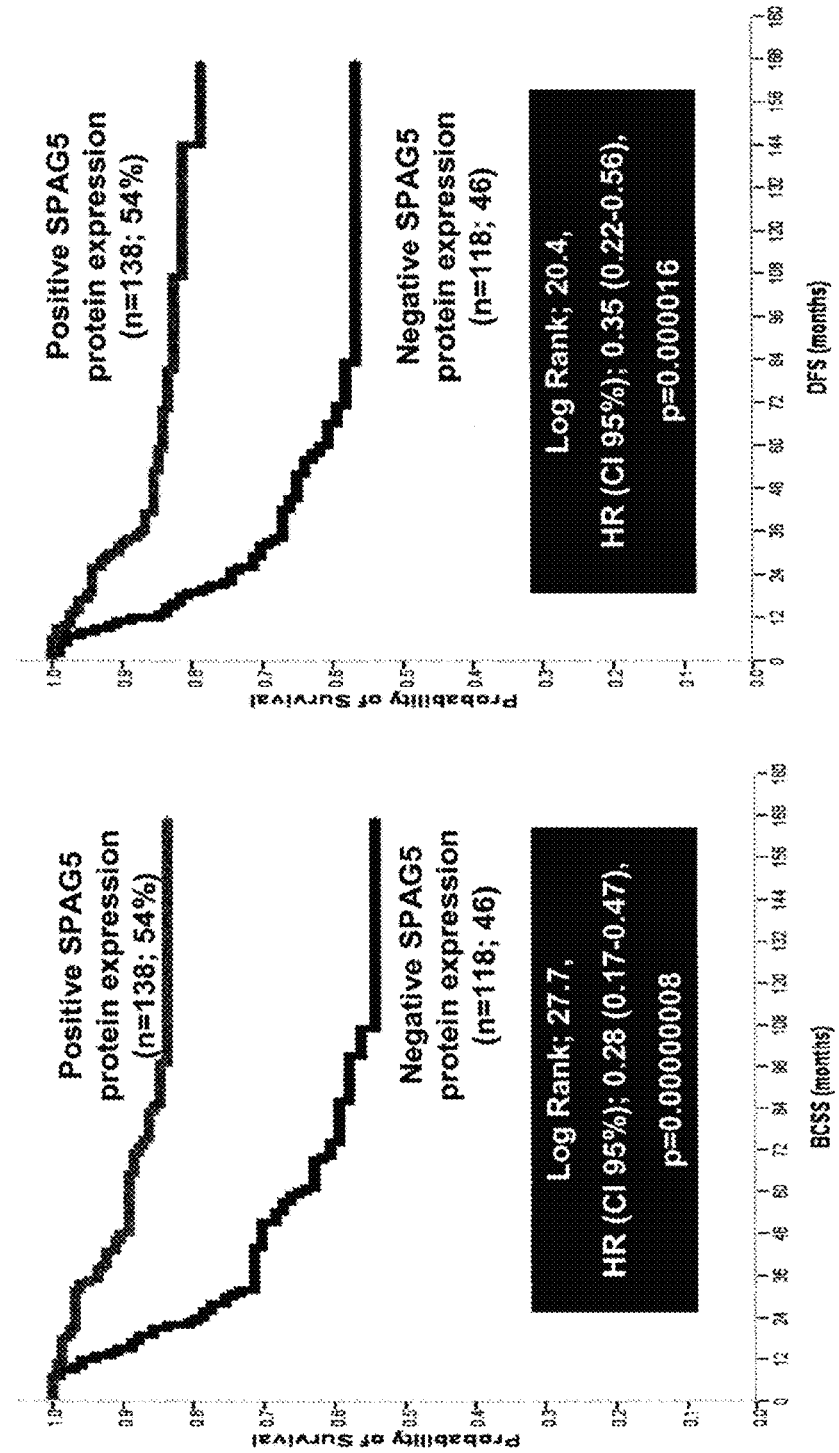

FIG. 12: Shows clinical outcome of high risk ER– breast cancer patients who received adjuvant anthracycline (n=256).

Figure 13:
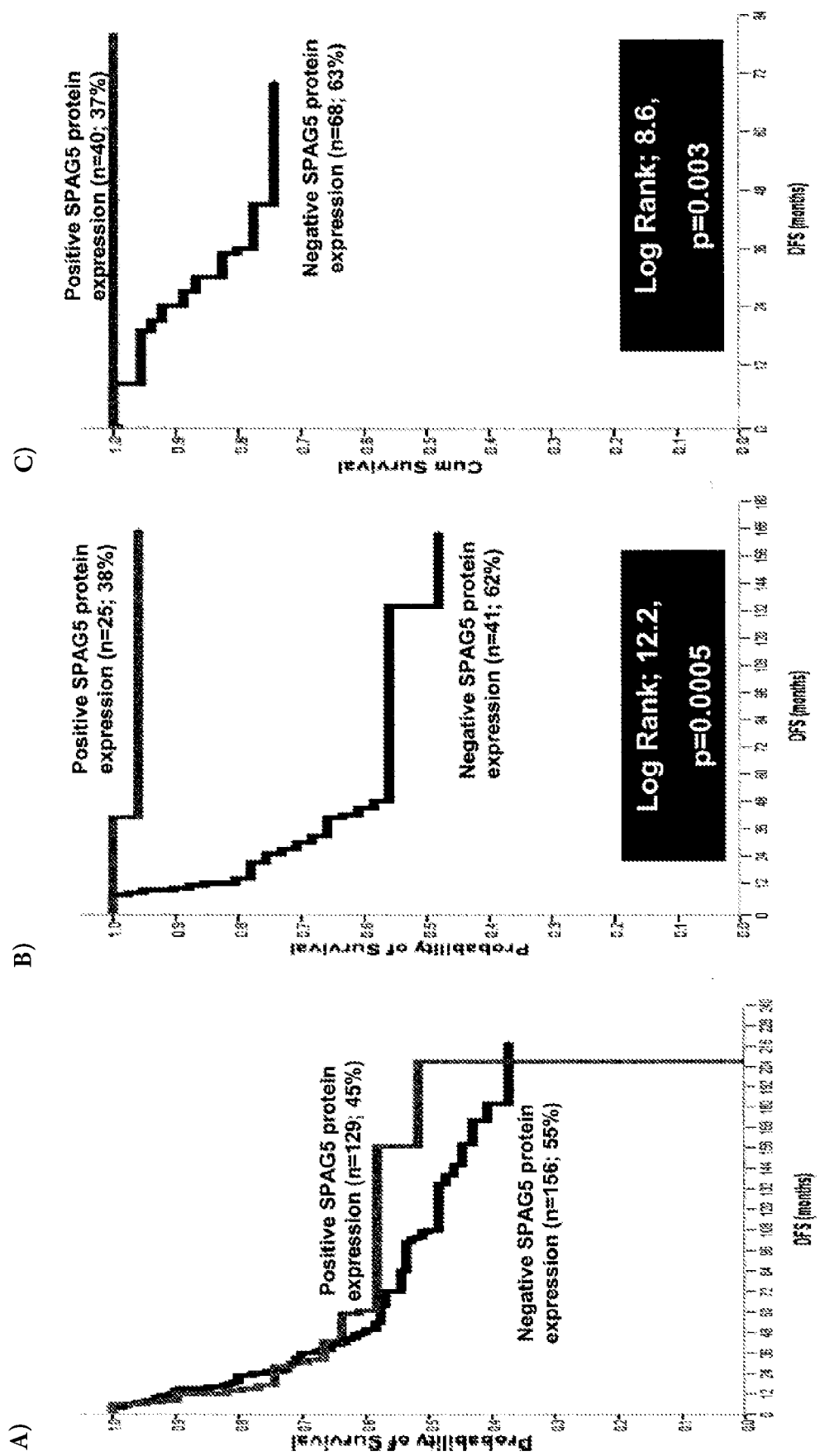

FIG. 13: Shows A) clinical outcome of patients with high risk HER+ breast cancer who did not receive HERCEPTIN® (trastuzumab, anti-HER2 monoclonal antibody) and either received CMF or no chemotherapy (n=285), B) clinical outcome of patients with high risk HER+ breast cancer who received anthracycline only (n=66), and C) clinical outcome of patients with high risk HER+ breast cancer who received both anthracycline and HERCEPTIN® (trastuzumab, anti-HER2 monoclonal antibody) (n=108).

FIG. 14: Shows multivariate analysis that confirms Top2A protein as an independent predictor for pCR.

Figure 15:
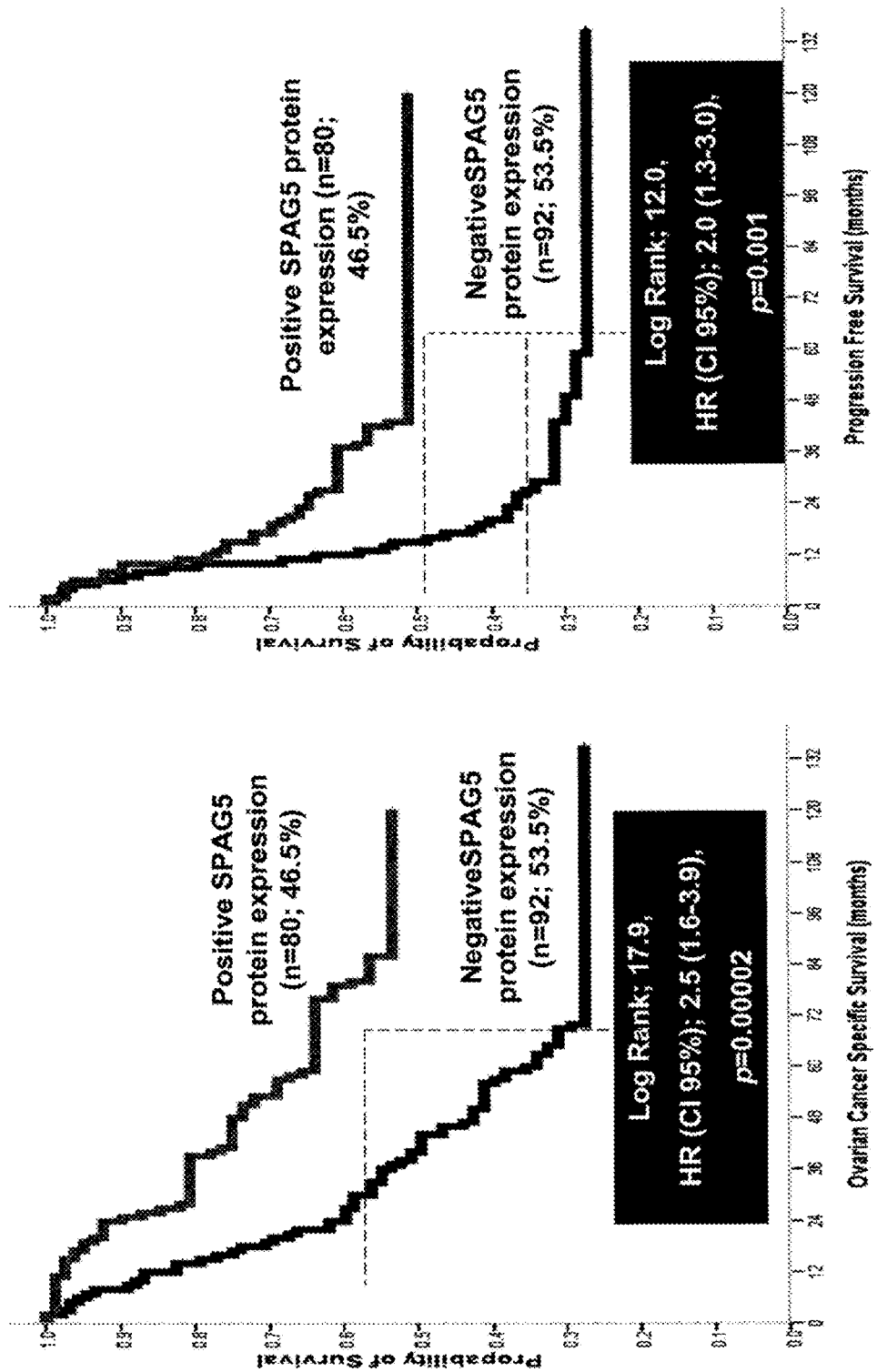

FIG. 15: Shows clinical outcome of a cohort of ovarian cancer patients having SPAG5 positive or SPAG5 negative tumours, FIG. 16: Shows Clinical outcome of mRNA SPAG5 in the gene expression discovery set (Nottingham series; n=128) and Clinical outcome of mRNA SPAG5 in the gene expression Confirmatory set (Uppsala series; n=249), FIG. 17: Shows Clinical outcome of Discovery set (n=128) and clinical outcome of the Nottingham set (n=1650) for each of the graphs Low expression and High expression refer to expression of SPAG5 protein.

Figure 18:
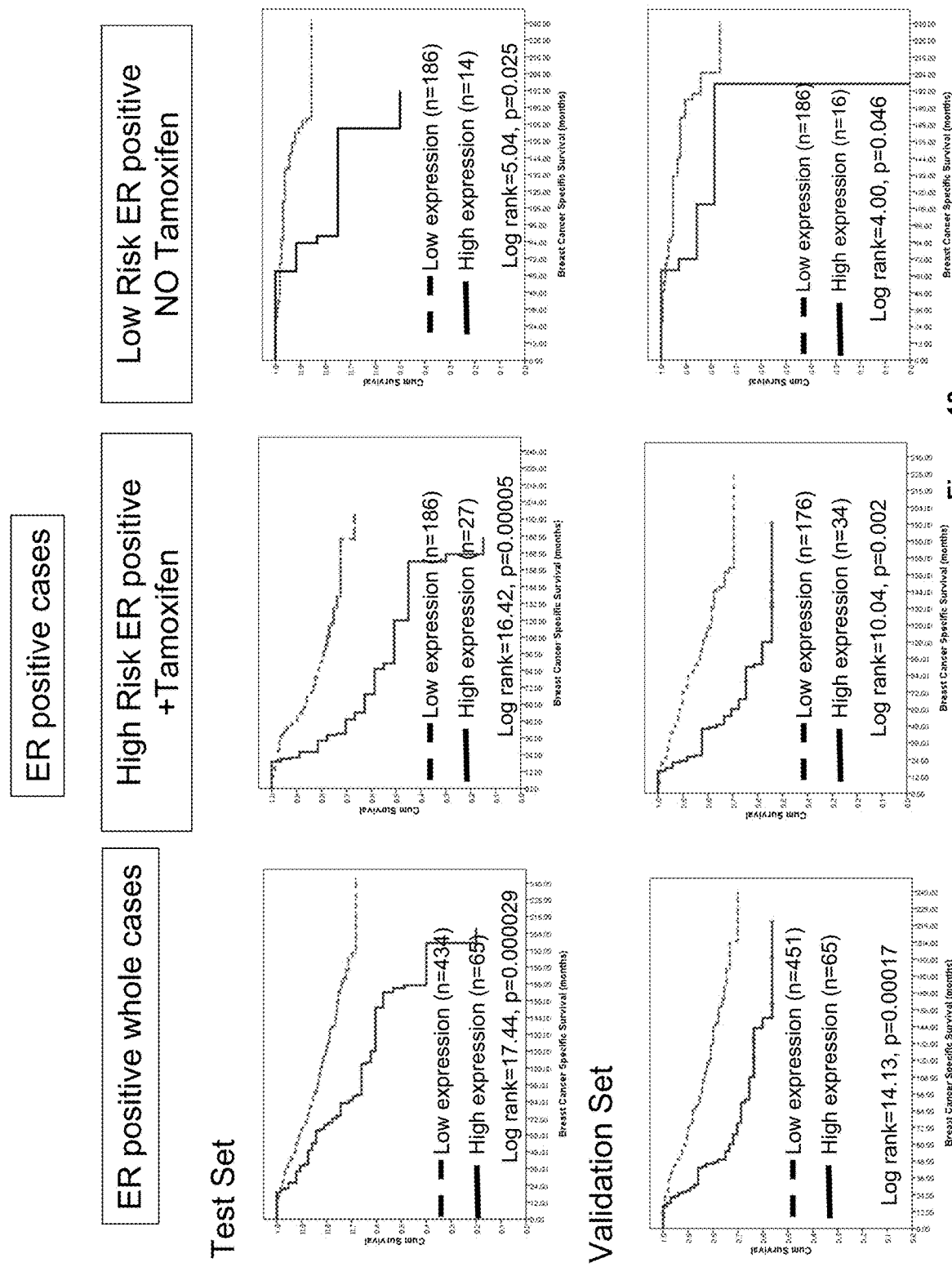

FIG. 18: Shows A comparison of the survival times for Estrogen Receptor (ER) positive breast cancer tumours for the test set (top row) and validation set (bottom row). For all breast cancer cases (left hand column); survival times for high risk Estrogen receptor (ER) positive tumours with Tamoxifen treatment (centre column) and survival times for low risk ER receptor positive tumours with no Tamoxifen treatment.

Figure 19:
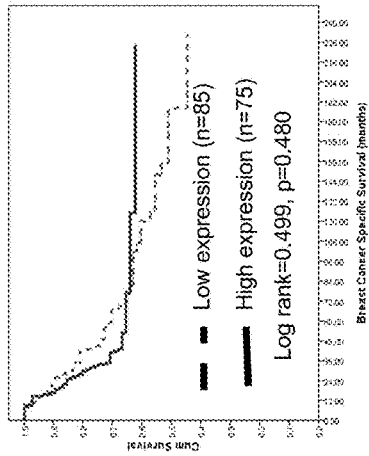
Figure 19:
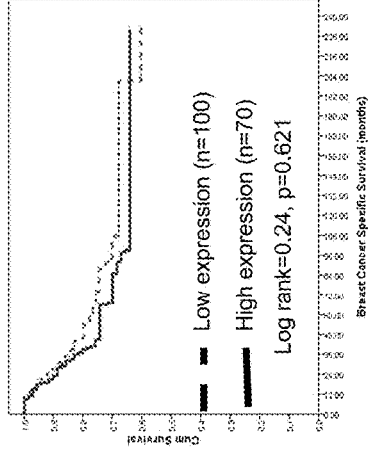
Figure 19:
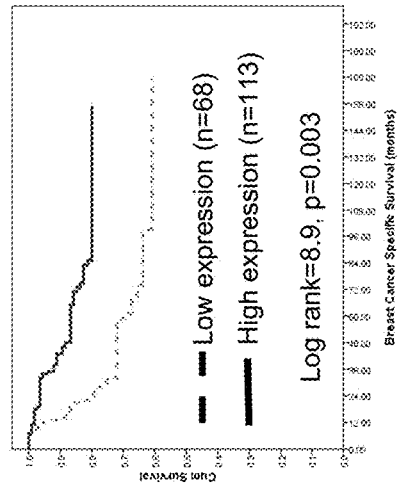
Figure 19:
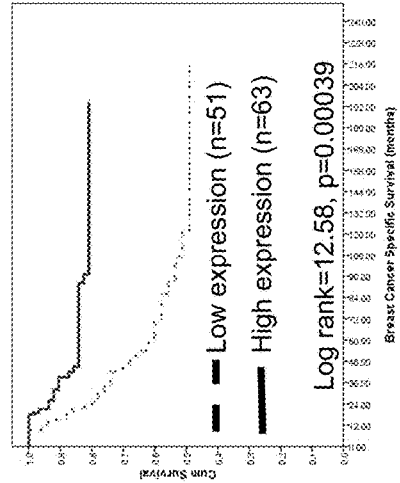
Figure 19:
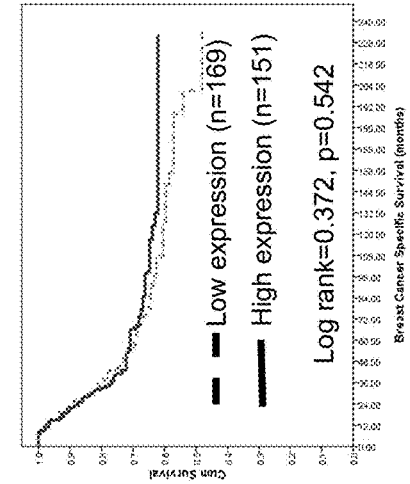

FIG. 19: Shows A comparison of the survival times for Estrogen Receptor (ER) negative breast cancer tumours for the test set (top row) and validation set (bottom row). Survival time is shown for high risk ER expressing tumours when no chemotherapy was used (bottom left); high risk ER expressing tumours with CMF chemotherapy and high risk ER expressing tumours when Anthracycline chemotherapy was used.

Figure 20:
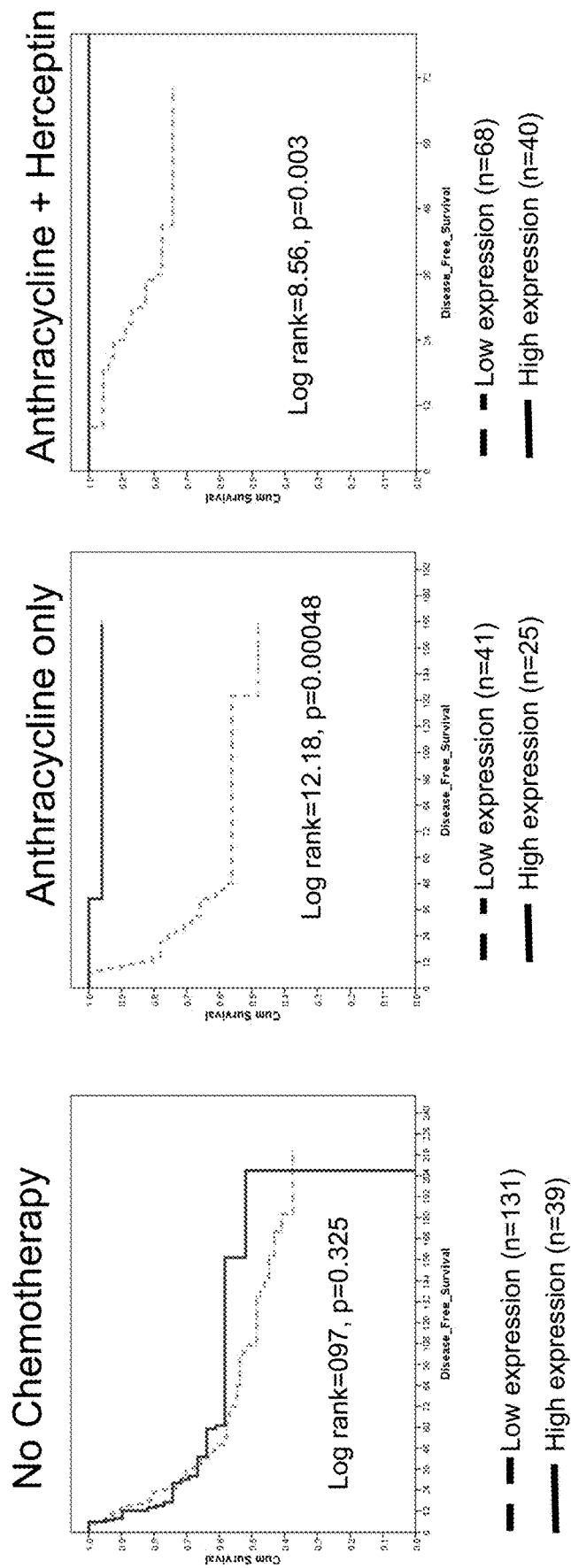

FIG. 20: Shows the survival times of patients with HER2 overexpressing breast cancer tumours with: no chemotherapy (left hand side), anthracycline only (centre) and anthracycline with HERCEPTIN® (trastuzumab, anti-HER2 monoclonal antibody) (right hand side).

Figure 21:
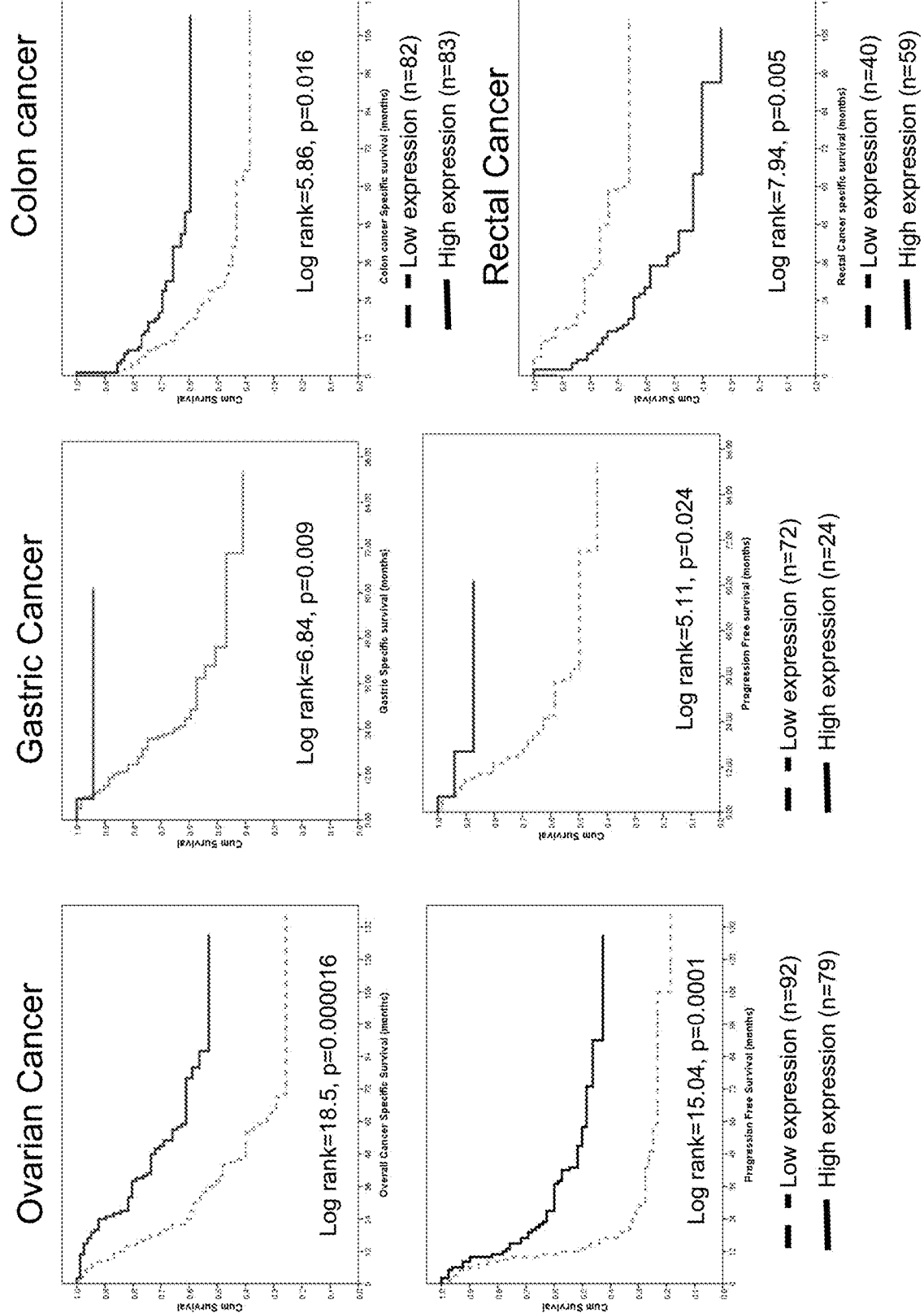

FIG. 21: Shows survival times for ovarian, gastric, colon and rectal cancers for patients with tumours that have high SPAG 5 expression and patients that have low SPAG5 expression, FIG. 22: Shows clinico-pathological correlations of SPAG5 protein expression in both the Training and Test sets, FIG. 23: Shows A comparison between the clinico-pathological characteristics of the Training and Validation sets showing both sets were well balanced, FIG. 24: Shows a list of the top 100 genes that are most closely associated with SPAG 5 in breast cancer tumours that over express estrogen receptors (ER+);

FIG. 25: Shows a list of the top 100 genes that are most closely associated with SPAG 5 in all breast cancers regardless of ER, PR and HER2 status of the tumours.

FIG. 26: Shows a list of the top 100 genes that are most closely associated with SPAG 5 in all breast cancers.

Expression of Sperm-associated antigen 5 (SPAG 5) in human cancer can be used as a prognostic, predictive and new therapeutic target for human cancers including breast, ovarian, gastric, and colorectal and pancreatic cancers.

Patients and Methods:

Study Patients

A) Breast Cancer

A retrospective study was carried out in a consecutive series of 2800 BC patients with primary operable invasive BCs who were diagnosed and treated in a single centre (Nottingham City Hospital) from 1990 to 2010 and constituted three cohorts:

1) Nottingham Tenovus Primary BC Treated from 1986 to 1998 (Nottingham/Tenovus Series):

This is a consecutive series of 1650 patients with primary invasive breast carcinomas who were diagnosed between 1989 and 1999 and entered into the Nottingham Tenovus Primary Breast Carcinoma series. This is a well-characterized series of patients under the age of 71 years (median=55 years) with long-term follow-up data (Supplemental Table S1). All patients were treated uniformly in a single institution and have been investigated in a wide range of biomarker studies. Patient characteristics such as age, family history, and menopausal status, and pathology characteristics such histologic grade, histologic tumor type, tumor size, lymph node stage, Nottingham Prognostic Index (NPI), and vascular invasion were routinely assessed in this large cohort (Pinder et al., Histopathology 24:41-7, 1994). Patients received standard surgery (mastectomy or wide local excision) with radiotherapy. Prior to 1989, patients did not receive systemic adjuvant treatment (AT). After 1989, AT was scheduled based on prognostic and predictive factor status, including NPI, oestrogen receptor-a (ER-a) status, and menopausal status. Patients with NPI scores of <3.4 (low risk) did not receive AT. In pre-menopausal patients with NPI scores of ≥3.4 (high risk), classical Cyclophosphamide, Methotrexate, and 5-Flourouracil (CMF) chemotherapy was given; patients with ER-a positive tumours were also offered HT. Postmenopausal patients with NPI scores of ≥3.4 and ER-a positivity were offered HT, while ER-α negative patients received classical CMF chemotherapy. Median follow up was 111 months (range 1 to 233 months).

TABLE S1

Clinicopathological characteristics of whole cohort (N = 1650)

| Variable | n* | Cases | (%) |
|---|---|---|---|
| Menopausal status | 1650 | | |
| Pre-menopausal | | 612 | (37.0) |
| postmenopausal | | 1038 | (63.0) |
| Tumor Grade (NGS) | 1650 | | |
| G1 | | 306 | (18.5) |
| G2 | | 531 | (32.2) |
| G3 | | 813 | (49.3) |
| Lymph node stage | 1650 | | |
| Negative | | 1056 | (64.0) |
| Positive (1-3 nodes) | | 486 | (29.5) |
| Positive (>3 nodes) | | 108 | (6.5) |
| Tumour size (cm) | 1650 | | |
| T1 a + b (≤1.0) | | 187 | (11.0) |
| T1 c (>1.0-2.0) | | 868 | (53.0) |
| T2 (>2.0-5) | | 5729 | (35.0) |
| T3 (>5) | | 16 | (1.0) |
| Tumour type | 1650 | | |
| IDC-NST | | 941 | (57) |
| Tubular | | 349 | (21) |
| ILC | | 160 | (10) |
| Medullary (typical/atypical) | | 41 | (2.5) |
| Others | | 159 | (9.5) |
| NPI subgroups | 1650 | | |
| Excellent PG (2.08-2.40) | Low risk | 207 | (12.5) |
| Good PG (2.42-3.40) | | 331 | (20.1) |
| Moderate I PG (3.42 to 4.4) | High risk | 488 | (29.6) |
| Moderate II PG (4.42 to 5.4) | | 395 | (23.9) |
| Poor PG (5.42 to 6.4) | | 170 | (10.3) |
| Very poor PG (6.5-6.8) | | 59 | (3.6) |
| Survival at 20 years | 1650 | | |
| Alive and well | | 1055 | (64.0) |
| Dead from disease | | 468 | (28.4) |
| Dead from other causes | | 127 | (7.6) |
| Adjuvant systemic therapy (AT) | 1602 | | |
| No AT | | 665 | (42.0) |
| Hormone therapy (ET) | | 642 | (41.0) |
| Chemotherapy | | 307 | (20.0) |
| Hormone + chemotherapy | | 46 | (3.0) |
| HAGE expression | 1650 | | |
| No staining (0) | normal | 1581 | |
| Strong (+++) | positive | 134 | |

*Number of cases for which data were available.
NPI; Nottingham prognostic index,
PG; prognostic group 2) Anthracycline Adjuvant Series:

256 primary invasive BC diagnosed and managed between 1998 and 2007 and all patients were primarily treated with surgery followed by radiotherapy and anthracycline-based chemotherapy 3) HER2+/HERCEPTIN® (Trastuzumab, Anti-HER2 Monoclonal Antibody) Adjuvant Series 140 primary BC HER2+ patients diagnosed and managed between 2005 and 2011 and all patients were primarily treated with surgery followed by radiotherapy and subsequent treatment with anthracycline-based and HERCEPTIN® (trastuzumab, anti-HER2 monoclonal antibody) chemotherapy.

4) Anthracycline-Neoadjuvant Series

To validate SPAG5 as a predictor factor for anthracycline chemotherapy, 260 patients with locally advanced primary breast cancer treated with anthracycline-based combination followed by surgery were included and the pathological complete response (PCR) was used to evaluate the response to chemotherapy. The complete pathological response was defined as an absence of invasive carcinoma in both primary site and axillary lymph nodes.

FIGS. 16 to 20 and 22 to 25 relate to data collected from a discovery gene expression set (Nottingham series; n=128) and a confirmatory gene expression set (Uppsala set; n=249).

These datasets were used to investigate the clinical outcome in terms of survival time for patients with tumours that had high or low expression of SPAG 5 and high or low expression of estrogen receptors (ER). This data is set out in FIGS. 16 to 20 and 21 to 25. The datasets were used to evaluate how the expression level of SPAG 5 combined with the expression or not of estrogen receptors can be used to predict the prognosis of patients and be used to evaluate which tumours are likely to be sensitive to particular chemotherapeutic agents with or without Tamoxifen.

Figure 16:
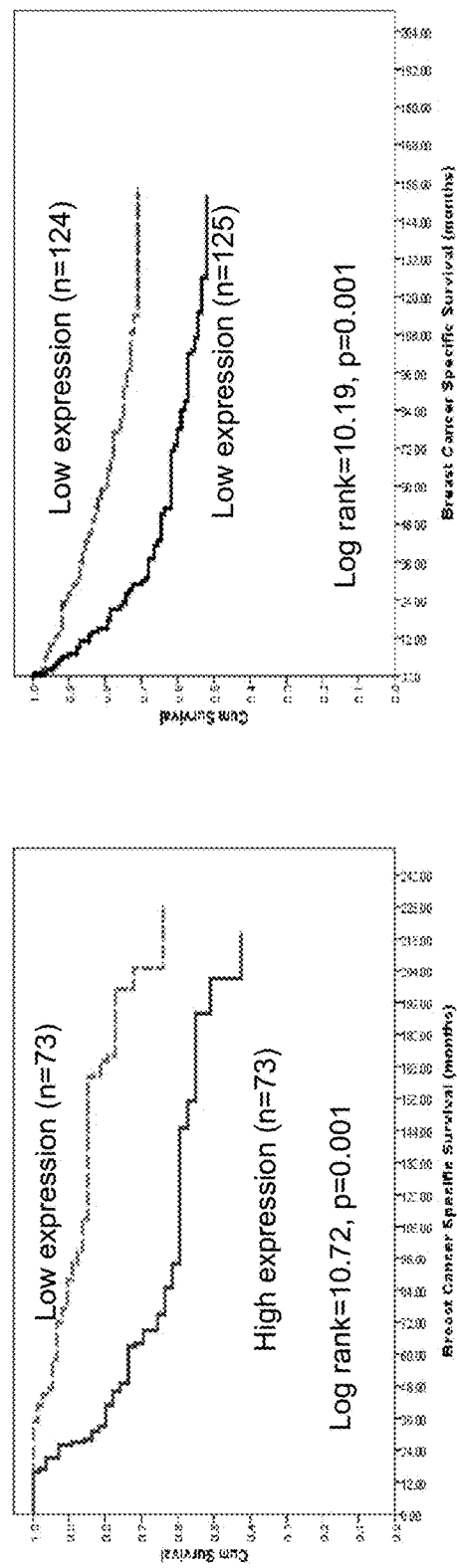
Figure 17:
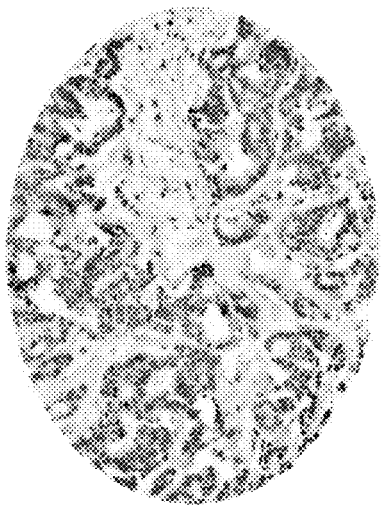
Figure 17:
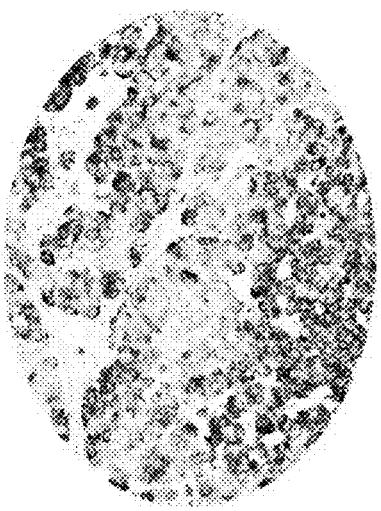
Figure 17:
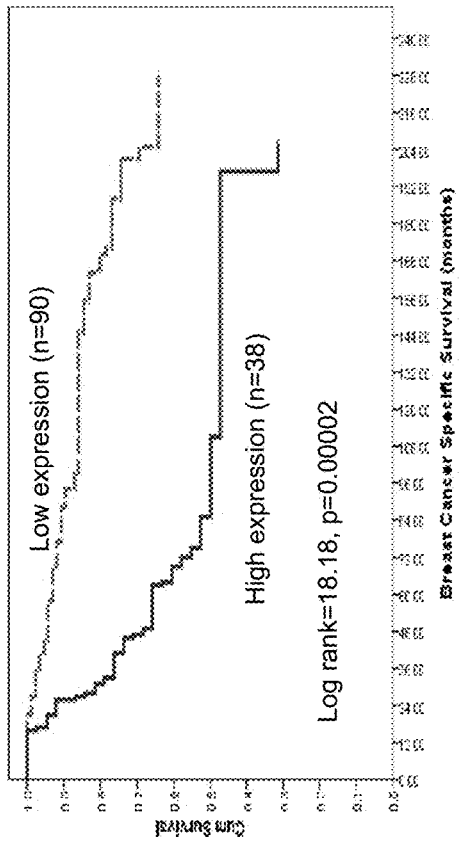
Figure 17:
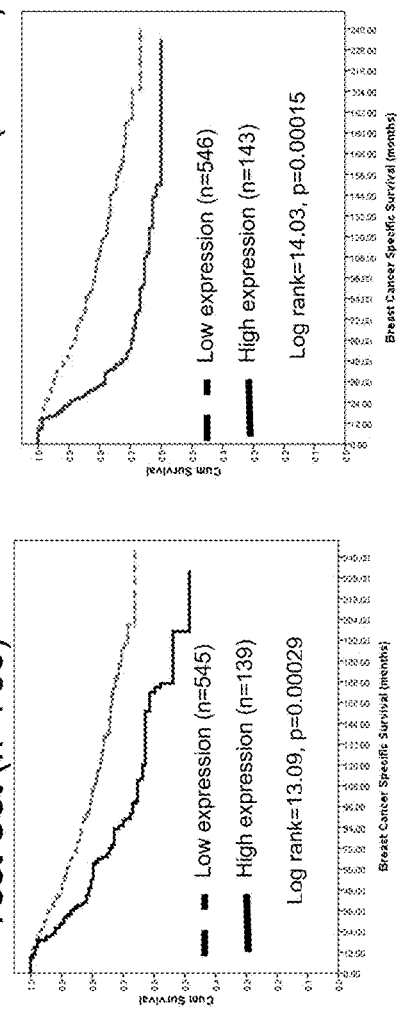

Overall, for all breast tumours, high expression of SPAG 5 correlated with poorer outcome (FIGS. 16 and 17).

For breast tumours that express estrogen receptors (ER+) low SPAG 5 expression correlated with better prognosis in terms of life expectancy than for ER+tumours that had high SPAG 5 expression. About 60% of breast cancers express estrogen receptors. The effect of using Tamoxifen for high risk and low risk ER+ tumours are shown in FIG. 18.

For breast tumours that do not express estrogen receptors (ER−) SPAG 5 expression is a less-strong predictor of survival time when chemotherapy is not applied. When chemotherapy with CMF or Anthracycline is applied tumours with high expression of SPAG 5 responded better to treatment as shown in FIG. 19.

Breast tumours that overexpress HER2 and also have over expression of SPAG 5 were shown to have a better prognosis if treated with anthracycline and HERCEPTIN® (trastuzumab, anti-HER2 monoclonal antibody) than when treated with anthracycline only. Patients whose breast tumours overexpressed SPAG 5 and HER2 had a good survival rate with treatment of anthracycline only and also with anthracycline and HERCEPTIN® (trastuzumab, anti-HER2 monoclonal antibody) as shown in FIG. 20.

High expression of SPAG 5 correlated with better prognosis in patients with ovarian, gastric and colon cancer but not in patients with rectal cancer see FIG. 21.

Tumours were graded as shown in FIGS. 22 and 23 which show that high expression of SPAG 5 at the gene level follows through to high SPAG 5 protein expression.

Assessment of the expression levels genes linked to SPAG 5 in different types of breast cancer, see genes listed in FIGS. 24 to 26, can help to understand the pathways that SPAG 5 is involved in different types of cancer cells. Gene "hubs", which are genes linked to a number of other genes in the SPAG 5 pathway, for example SPAG 5 itself, can be knocked out in model systems to test the effect on expression levels of the genes that are linked to SPAG 5. This can lead to better understanding of the pathways linked to SPAG 5.

B) Ovarian Cancer

Investigation of the expression of SPAG5 in ovarian cancer was carried out on a tissue microarray of 172 ovarian cancer cases. This cohort comprised of female patients with a median age of 61 years (range 33-87, mean 60 years). Of the 172 patients included in the study, 54 (34%) were dead before the end of the follow-up period. Histologically, most patients were found to have a serous cystadenocarcinoma (56%), followed by endometrioid (21%), clear cell carcinoma (13%), mucinous cystadenocarcinoma (8%) or other types (2%). Tumours displayed poor histologic differentiation in 73% of cases. The majority of tumours were classified as FIGO stage III (45%). Tissue was obtained from patients with primary ovarian cancer treated at Nottingham University Hospitals (NUH) between 2000 and 2007. Survival was calculated from the operation date until 1st of April 2009 when any remaining survivors were censored. During the study period, patients were treated with either single agent carboplatin [65 patients (41.4%)] or platinum-based combination chemotherapy [89 patients (56.7%); 79/89 patients received carboplatin and paclitaxel, 4/89 received Cyclophosphamide/Doxorubicin/Cisplatinum (CAP), 3/89 were treated in ICON-5 trial using paclitaxel, carboplatin plus gemcitabine or topotecan 29 and 3/89 were treated according to the SCOTROC trial protocol by carboplatin, docetaxel+/−topotecan 30. Platinum resistance was defined as patients who had progression during first-line platinum chemotherapy or relapse within 6 months after treatment.

The Reporting Recommendations for Tumor Marker Prognostic Studies (REMARK) criteria, recommended by McShane et al, J. Natl Cancer Inst 97:1180-4, 2005, were followed throughout this study. This work was approved by Nottingham Research Ethics Committee.

Survival Data

Survival data including survival time, disease-free survival (DFS), and development of loco-regional and distant metastases (DM) were maintained on a prospective basis. DFS was defined as the number of months from diagnosis to the occurrence of local recurrence, local LN relapse or DM relapse. BC specific survival (BCSS) was defined as the number of months from diagnosis to the occurrence of BC related-death. DM-free survival was defined as the number of months from diagnosis to the occurrence of DM relapse. Survival was censored if the patient was still alive, lost to follow-up, or died from other causes.

Immunohistochemistry (IHC)

Tumours from Nottingham/Tenovus series, HER2/HERCEPTIN® (trastuzumab, anti-HER2 monoclonal antibody), Anthracycline-adjuvant and ovarian cancer series were arrayed in tissue microarrays (TMAs) constructed with 2 replicate 0.6 mm cores from the centre and periphery of the tumors for each patient. While full-face sections from pre-chemotherapy core biopsy of Anthracycline-Neoadjuvant series were used. The TMAs and full face sections were immunohistochemically profiled for SPAG5 and other biological antibodies (Table 5) as previously described (9-12). Immunohistochemical staining was performed using NOVOLINK Detection kit according to the manufacturer instructions (Leica Microsystems). Sections were incubated for 30 mins at room temperature with 1/50 Anti-SPAG5 rabbit polyclonal (HPA022479; Sigma). Anti-SPAG5 antibody produced in rabbit, a Prestige Antibody, is developed and validated by the Human Protein Atlas (HPA) project (www.proteinatlas.org) where the antibody is tested by immunohistochemistry against hundreds of normal and disease tissues.

Pre-treatment of sections was performed with citrate buffer (pH 6.0) antigen for 20 minutes. To validate the use of TMAs for immuno-phenotyping, full-face sections of 40 cases were stained and the protein expression levels of the different antibodies were compared. The concordance between TMAs and full-face sections was excellent (kappa=0.8). Positive and negative (omission of the primary antibody and IgG-matched serum) controls were included in each run.

Evaluation of Immunohistochemical Staining

The tumour cores were evaluated by three pathologists of co-authors blinded to the clinico-pathological characteristics of patients in two different settings. There was excellent intra and inter-observer agreements (k>0.8; Cohen's κ and multi-rater κ tests, respectively). Whole field inspection of the core was scored and intensities of cytoplasmic staining were grouped as follows: 0=no staining, 1=weak staining, 2=moderate staining, 3=strong staining. The percentage of each category was estimated. Positive SPAG5 (SPAG5+) expression was defined as the presence of granular cytoplasmic staining in >10% of malignant cells. Not all cores within the TMA were suitable for IHC analysis as some cores were missing or lacked tumour.

Statistical Analysis

Data analysis was performed using SPSS (SPSS, version 17 Chicago, Ill.). Where appropriate, Pearson's Chi-square, Fisher's exact, Student's t and ANOVAs one way tests were used. Cumulative survival probabilities were estimated using the Kaplan-Meier method and differences between survival rates were tested for significance using the log-rank test. Multivariate analysis for survival was performed using the Cox hazard model. The proportional hazards assumption was tested using standard log-log plots. Hazard ratios (HR) and 95% confidence intervals (95% CI) were estimated for each variable. All tests were two-sided with a 95% CI and a p value of <0.05 considered significant. For multiple comparisons, p values were adjusted according to Holm-Bonferroni correction method (13).

Results i) 15% and 5% of BC showed gain and amplification of SPAG5 locus, respectively, at chromosome 17q11.2. SPAG5 mRNA expression levels displayed a statistically significant correlation with its copy number (p=0.01), ii) 30% and 20% of ovarian and breast cancer showed SPAG5 protein over-expression, iii) In breast cancer, SPAG5 overexpression at both mRNA and protein levels showed a statistically significant association with ER−, PR−, triple negative phenotype, high grade tumour, high mitotic index, high ki67, high KIF2C, basal like phenotype and epithelial mesenchymal transition (EMT) phenotype, p53 and absence of DNA repair genes (BRCA1, ATM and XRCC1); p values<0.0001, iii) SPAG5 mRNA overexpression was statistically associated with poor clinical outcome (p<0.0001). In ER− BC who treated with S+RT followed by anthracycline based adjuvant chemotherapy, SPAG5 negative BC had 7-10 times risk death, progression and DM (p values<0.00001). Moreover, in locally advanced BC who received anthracycline-bases neoadjuvant chemotherapy, SPAG5 overexpression BC achieved 38% pCR vs., 7% of SPAG5-negative BC (p<0.00001). After controlling to other validated predictors for pCR, SPAG5 remained as a powerful independent predictor (HR; 2.4, CI 95%; 1.5-3.9; p=0.00001). vi) SPAG5 negative OVC were resistant to platinum chemotherapy (p=0.004) and SPAG5 negative expression had 3 fold increase of risk of death (p=0.008) and progression (p=0.001) and independently associated with poor survival [HR 2.6, p=0.008].

Neural network (NNT) and pathways analysis of a breast cancer (BC) gene expression array data from 128 patients showed that that SPAG5 was among top 10 ranked genes out of 48,000 transcripts, that accurately predicted worse clinical outcome, differentiated between low and high grade cancers and distinguished between breast cancer with high mitotic index and breast cancer with low mitotic index. These results were based on a 10-fold external cross-validation analysis with an average classification accuracy of >99.999%. SPAG5 was identified as a major hub in the KIF2C pathway and its expression is strongly related to expression of genes that are involved in mitotic cell cycle regulation (FIG. 1).

Dual immunoflorescent staining (IF) in breast cancer cell lines (FIG. 4) showed co-expression of SPAG5 and proliferating cell nuclear antigen (PCNA) in 4 out of 5 of the breast cancer cell lines screened (MCF7, T47D, MDA468 and MDA231). In these breast cancer cells the IF staining strongly suggested that in proliferating cells (evidenced by PCNA staining) there is both co-expression of SPAG5 and PCNA as well as increased levels of expression of SPAG5 providing evidence for the importance of SPAG5 in cell proliferation. Furthermore there is evidence of localisation of SPAG5 within the centrosomes and spindles of dividing cells.

The molecular and clinicopathological functions of SPAG5 expression and its effect on management of both breast and ovarian cancers (OVC) have been investigated.

SPAG5 may be over-expressed in breast, ovarian, gastric, pancreatic and colorectal cancer tissues. Tumours that over express SPAG5 (SPAG5+ tumours) are associated with more aggressive highly proliferating breast and ovarian cancer. Moreover, it is possible from the amount of SPAG5 expression to identify patients who should be clinically treated in particular ways and could be a target for new therapeutics.

If a tumour over expresses SPAG5 it indicates an increased probability that the cancer is aggressive. Tumours that overexpress SPAG5 were also shown to have a greater chance of response to chemotherapy with anthracycline adjuvant therapy, adjuvant therapy with HERCEPTIN® (trastuzumab, anti-HER2 monoclonal antibody) and anthracycline and neoadjuvant therapy with anthracycline. SPAG5 expression may be determined by staining tissue samples with labelled SPAG5-specific antibodies (FIG. 6). The presence of strong granular cytoplasmic expression in >10% of the malignant cells indicates overexpression of SPAG5 (SPAG5+). The normal breast tissues showed weak SPAG5 expression (SPAG5−). Normal spleen, smooth muscle, colon, prostate and bladder tissues also usually show weak SPAG5 expression.

By using high resolution array comparative genomic hybridization (aCGH) using data from the Chin et al database (Chin et al, Genome Biol 207; 8:R215) it was shown that between 5% and 15% of breast cancers showed amplification and gain of SPAG5 locus, respectively, at 17q11.2. SPAG5 mRNA expression displayed a significant correlation with its copy number ($p<0.0001$).

Clinicopathological Features of SPAG5 mRNA Expression

SPAG5 mRNA high expression (mRNA SPAG5+) was significantly associated with aggressive clinico-pathological features including: ER−, high grade, high proliferation index, triple receptor negative (TNT) phenotypes, overexpression of HER2 and p53 mutation (Table 1). In multivariate regression analysis mRNA SPAG5 level was only associated with ER− and high mitoses (FIG. 5). Moreover, mRNA SPAG5+ patients have 2-3-time increased risk of deaths and recurrence in the long term, compared to mRNA SPAG5-cases (FIG. 2).

TABLE 1

Association between SPAG5 mRNA expression and other clinico-pathologic variables

| | SPAG5 mRNA Expression | | |
|---|---|---|---|
| Variable | Low (N = 73) n (%) | High (N = 55) n (%) | $X^2$ Adjusted p value |
| A) Pathological Parameters | | | |
| Tumor Size | | | 0.02 |
| T1 a + b (≤1.0) | 8 (13) | 2 (4) | |
| T1 c (>1.0-2.0) | 40 (64) | 25 (516) | |
| T2 (>2.0-5) | 14 (23) | 22 (22) | |
| T3 (>5) | 0 (0) | 0 (0) | |
| Lymph node stage | | | |
| Negative | 56 (77) | 30 (55) | 0.028 |
| Positive (1-3 nodes) | 15 (20) | 21 (38) | |
| Positive (>3 nodes) | 2 3) | 4 (7) | |
| Grade** | | | 0.000000009 |
| G1 | 30 (41) | 2 (4) | |
| G2 | 31 (43) | 22 (40) | |
| G3 | 12 (16) | 31 (56) | |
| Mitotic Index | | | 0.0000000004 |
| M1 (low; mitoses < 10) | 41 (66) | 4 (8) | |
| M2 (medium; mitoses 10-18) | 14 (23) | 16 (33) | |
| M3 (high; mitosis > 18) | 7 (11) | 29 (59) | |
| Pleomorphism | | | 0.001* |
| 1 (small-regular uniform) | 5 (8) | 1 (2) | |
| 2 (Moderate variation) | 41 (661) | 18 (37) | |
| 3 (Marked variation) | 16 (26) | 30 (611) | |
| B) Hormonal receptors | | | |
| ER | | | 0.000002 |
| (Negative) | 10 (14) | 29 (53) | |
| (Positive) | 63 (86) | 26 (47) | |
| PR | | | 0.001* |
| (Negative) | 16 (28) | 28 (61) | |
| (Positive) | 41(72) | 18 (39) | |
| Cell cycle/apoptosis regulators | | | |
| p53 | | | 0.0000005* |
| (Negative) | 56 (98) | 29 (59) | |
| (Positive) | 1 (2) | 20 (41) | |
| EGFR | | | 0.015* |
| (Negative) | 47 (87) | 30 (67) | |
| (Positive) | 7 (13) | 15 (33) | |
| vimentin | | | 0.007* |
| (Negative) | 38 (97) | 30 (77) | |
| (Positive) | 1 (3) | 9 (23) | |
| Bcl2 | | | 0.000002 |
| (Negative) | 16 (26) | 35 (71) | |
| (Positive) | 46 (74) | 14 (29) | |
| Ki67 | | | 0.00000002 |
| (Negative) | 33 (85) | 8 (21) | |
| (Positive) | 6 (15) | 30 (79) | |
| p16 | | | 0.0004* |
| (Negative) | 41 (100) | 27 (73) | |
| (Positive) | 0 (0) | 10 (27) | |
| Aggressive phenotype | | | |
| Her2 overexpression | | | 0.006* |
| (No) | 58 (97) | 36 (80) | |
| (Yes) | 2 (3) | 9 (20) | |
| Triple negative | | | 0.0002* |
| (No) | 58 (95) | 32 (68) | |
| (Yes) | 3 (5) | 15 (32) | |

TABLE 1-continued

Association between SPAG5 mRNA expression and other clinico-pathologic variables

| Variable | SPAG5 mRNA Expression | | $X^2$ Adjusted p value |
|---|---|---|---|
| | Low (N = 73) n (%) | High (N = 55) n (%) | |
| Basal like | | | 0.02 |
| (No) | 57 (93) | 37 (79) | |
| (Yes) | 4 (7) | 10 (21) | |

**grade as defined by NGS;
BRCA1: BC 1, early onset;
HER2: human epidermal growth factor receptor 2;
ER: oestrogen receptor;
PR: progesterone receptor;
CK: cytokeratin;
Basal-like: ER-, HER2 and positive expression of either CK5/6, CK14 or EGFR;
Triple negative: ER-/PR-/HER2-

Clinicopathological feature of SPAG5 protein expression 20% of breast cancer showed SPAG5 protein overexpression. SPAG5 overexpression showed a statistically significant association with ER−, PR−, triple negative phenotype, high grade tumour, high mitotic index, high ki67, high KIF2C, basal like phenotype and epithelial mesenchymal transition (EMT) phenotype, p53 and absence of DNA repair genes (BRCA1, ATM and XRCC1); p values<0.0001 (Table 2). In multivariate regression analysis model, ER, mitotic index and p16 mutation were are only markers independently associated with SPAG5 overexpression (FIG. 10).

TABLE 2

Association between SPAG5 protein expression and other clinico-pathologic variables in BC

| Variable | | SPAG5 protein Expression | | $X^2$ Adjusted p value |
|---|---|---|---|---|
| | | Low (N = 1125) n (%) | High (N = 259) n (%) | |
| A) Pathological Parameters | | | | |
| Tumor Size | | | | 0.110 |
| T1 a + b (≤1.0) | | 107 (11) | 16 (7) | |
| T1 c (>1.0-2.0) | | 510 (53) | 121 (51) | |
| T2 (>2.0-5) | | 337 (35) | 95 (40) | |
| T3 (>5) | | 4 (1) | 4 (2) | |
| Lymph node stage | | | | 0.188 |
| Negative | | 612 (63) | 136 (57) | |
| Positive (1-3 nodes) | | 293 (30) | 86 (36) | |
| Positive (>3 nodes) | | 67 (7) | 15 (6) | |
| Grade** | | | | $2 \times 10^{-22}$ |
| G1 | | 196 (20) | 13 (5.5) | |
| G2 | | 356 (37) | 36 (15) | |
| G3 | | 418 (43) | 187 (79) | |
| Mitotic Index | | | | $1.5 \times 10^{-23}$ |
| M1 (low; mitoses < 10) | | 401 (41) | 32 (14) | |
| M2 (medium; mitoses 10-16) | | 194 (20) | 26 (11) | |
| M3 (high:, mitosis > 18) | | 375 (39) | 178 (75) | |
| Pleomorphism | | | | $4.3 \times 10^{-21}$* |
| 1 (small-regular uniform) | | 27 (3) | 2 (1) | |
| 2 (Moderate variation) | | 445 (46) | 31 (13) | |
| 3 (Marked variation) | | 498 (51) | 203 (86) | |
| B) Hormonal receptors | | | | |
| ER | (Negative) | 176 (20) | 136 (61) | $1.6 \times 10^{-34}$ |
| | (Positive) | 714 (80) | 87 (39) | |
| PR | (Negative) | 343 (37) | 156 (69) | $1.0 \times 10^{-17}$* |
| | (Positive) | 578 (63) | 71 (31) | |
| AR | (Negative) | 296 (31) | 137 (65) | $2.8 \times 10^{-20}$* |
| | (Positive) | 607 (69) | 74 (35) | |
| JNK | (Negative) | 504 (52) | 82 (59) | 0.0000005* |
| | (Positive) | 463 (48) | 158 (41) | |
| Bcl2 | (Negative) | 299 (30) | 132 (55) | $5.1 \times 10^{-42}$ |
| | (positive) | 709 (70) | 109 (45) | |
| Tumour type | | | | |
| IDC | | 525 (54) | 173 (75) | $1.6 \times 10^{-19}$ |
| Tubular | | 218 (23) | 24 (10) | |
| Medullary | | 11 (1) | 20 (9) | |
| ILC | | 114 (12) | 7 (3) | |
| others | | 98 (10) | 7 (3) | |
| XRCC1 | (Negative) | 132 (14) | 61 (26) | $4.5 \times 10^{-6}$ |
| | (positive) | 823 (86) | 172 (74) | |
| HAGE | (Negative) | 1000 (93) | 218 (86) | $4.7 \times 10^{-4}$ |
| | (Positive) | 79 (7) | 36 (14) | |
| P53 | (Negative) | 756 (85) | 140 (64) | $9.9 \times 10^{-13}$ |
| | (Positive) | 135 (15) | 80 (36) | |
| KIF2C | (Negative) | 198 (25) | 30 (16) | 0.006 |
| | (Positive) | 601 (75) | 164 (84) | |
| MIB1 | (low) | 278 (49) | 25 (23) | $2.4 \times 10^{-7}$ |
| | (high) | 284 (51) | 91 (77) | |
| TOP2A | (negative) | 390 (47) | 98 (47) | 0.9 |
| | (High) | 438 (53) | 112 (53) | |
| Ck5/6 | (negative) | 820 (88) | 157 (68) | $1.1 \times 10^{-13}$ |
| | (positive) | 112 (12) | 74 (32) | |
| EGFR | (negative) | 709 (82) | 156 (72) | 0.001 |
| | (positive) | 154 (18) | 60 (23) | |
| BRCA1 | (Loss) | 124 (16) | 60 (31) | $4.1 \times 10^{-6}$ |
| | (positive) | 649 (84) | 137 (69) | |
| P21 | (Negative) | 432 (64) | 147 (68) | $2.2 \times 10^{-4}$ |
| | (positive) | 363 (46) | 68 (32) | |
| P16 | (Negative) | 717 (92) | 136 (66) | $4.7 \times 10^{-22}$ |
| | (Positive) | 65 (8) | 71 (34) | |
| MDM2 | (negative) | 562 (72) | 190 (89) | $3.3 \times 10^{-7}$ |
| | (positive) | 215 (28) | 23 (11) | |
| CK14 | (negative) | 819 (89) | 192 (83) | 0.01 |
| | (positive) | 102 (11) | 40 (17) | |
| Basal like | (No) | 850 (92) | 142 (65) | $4.3 \times 10^{-27}$ |
| | (Yes) | 74 (8) | 78 (35) | |
| Vimentine | (Negative) | 597 (94) | 120 (70) | $3.6 \times 10^{-18}$ |
| | (positive) | 41 (6) | 52 (30) | |
| SMA | (Negative) | 816 (89) | 179 (79) | $2.6 \times 10^{-5}$ |
| | (Positive) | 98 (11) | 48 (21) | |
| P63 | (Negative) | 906 (99) | 219 (96) | 0.001 |
| | (Positive) | 11 (1) | 10 (4) | |
| CK18 | (negative) | 64 (7) | 53 (25) | $1.4 \times 10^{-13}$ |
| | (positive) | 807 (93) | 160 (75) | |
| CK 19 | (negative) | 43 (5) | 30 (13) | $3.1 \times 10^{-6}$ |
| | (positive) | 883 (95) | 202 (87) | |
| P-Cadherin | (negative) | 415 (53) | 53 (27) | $3.3 \times 10^{-11}$ |
| | (positive) | 366 (47) | 145 (73) | |
| FIHT | (negative) | 148 (18) | 61 (31) | $7.6 \times 10^{-5}$ |
| | (positive) | 677 (82) | 139 (69) | |
| ATM | (negative) | 136 (40) | 49 (55) | 0.01 |
| | (Positive) | 201 (60) | 40 (45) | |
| Tubular formation | | | | $3.9 \times 10^{-7}$ |
| T1 | | 62 (6) | 2 (1) | |
| T2 | | 354 (36) | 57 (24) | |
| T3 | | 554 (57) | 177 (75) | |
| T24 | (Negative) | 578 (72) | 170 (23) | 0.016* |
| | (Positive) | 220 (28) | 41 (19) | |

*Statistically significant;
**grade as defined by NGS;
BRCA1: BC 1, early onset;
HER2: human epidermal growth factor receptor 2;
ER: oestrogen receptor;
PR: progesterone receptor;
CK; cytokeratin;
Basal-like: ER-, HER2 and positive expression of either CK5/6, CK14 or EGFR;
Triple negative: ER-/PR-/HER2-

Clinical Outcome of SPAG5 Protein Expression

In high risk Estrogen receptor negative (ER−) breast cancer patients who did not received any adjuvant therapy or received ineffective CMF chemotherapy, tumours that overexpressed SPAG5 protein and tumours that did not overexpress SPAG5 had a similar risk of recurrence and the patients had a similar risk of death (FIG. 11). Receiving anthracycline chemotherapy had a positive impact on high risk ER− breast cancer patients with patients whose tumours over expressed SPAG5 protein having 72-65% less chance of death, recurrence and metastases compared to patients whose tumours did not overexpress SPAG5 protein; p<0.0001 (FIG. 12). The positive impact of anthracycline on patients with SPAG5+ tumours has also been shown for tumours that are HER2 positive (HER2+). These patients either received anthracycline only (treated before 2006) or anthracycline plus HERCEPTIN® (trastuzumab, anti-HER2 monoclonal antibody) (FIG. 13).

Patients with locally advanced breast cancer tumours who received anthracycline-based neoadjuvant chemotherapy had 39% pathological complete response (pCR) for SPAG5+ BC but only 6% pCR for SPAG5-negative BC (p<0.00001). After controlling to other validated predictors for pCR, SPAG5 remained as a powerful independent predictor (HR; 2.4, CI 95%; 1.5-3.9; p=0.00001).

Ovarian Cancer

In ovarian cancer, 46.5% of tumours showed SPAG5+ protein expression which was significantly associated with aggressive clinico-pathological features including higher stage; grade and clear cell histological subtype (Table 4). Moreover, SPAG5+ ovarian cancer tumours were more sensitive to platinum chemotherapy (p=0.002; Table 4) and had higher probability of pathological (p=015) and CA125 response (p=0.036). CA125 is a marker that is routinely used in practice to indicate the presence of ovarian cancer. In addition, SPAG5 negative expression had 3 fold increase of risk of death (p=0.00008) and progression and independently associated with poor survival [HR 2.6, p=0.001; FIG. 15].

TABLE 4

Association between SPAG5 protein expression and other clinico-pathologic variables in ovarian cancer

| Variable | SPAG5 Protein Expression | | $X^2$ Adjusted p value |
|---|---|---|---|
| | Low (N = 92) n (%) | High (N = 80) n (%) | |
| A) Pathological Parameters | | | |
| Cancer Stage | | | 0.004 |
| 0 | 1 (13) | 1 (1) | |
| I | 17 (64) | 36 (46) | |
| II | 14 (23) | 8 (10) | |
| III | 47 (51) | 29 (37) | |
| IV | 13 (14) | 5 (6) | |
| Optimal debunked | | | 0.008 |
| yes | 51 (55) | 61 (78) | |
| no | 41 (45) | 17 (22) | |
| Status of residual tumour burden | | | 0.015 |
| No residual | 26 (28) | 30 (38) | |
| microscopic | 17 (18) | 26 (33) | |
| <1 cm | 8 (9) | 3 (4) | |
| >1-2 cm | 8 (9) | 7 (9) | |
| >2 cm | 33 (36) | 13 (16) | |
| CA125 response | | | 0.036 |
| No response | 5 (6) | 3 (4) | |
| Complete response | 65 (76) | 64 (89) | |
| Partial response | 10 (12) | 3 (4) | |
| Steady response | 0 (0) | 2 (3) | |
| Progressive response | 5 (6) | 0 (0) | |
| Tumour type | | | 0.02 |
| Clear cell carcinoma | 5 (7) | 13 (20) | |
| Non clear carcinoma | 68 (93) | 52 (80) | |
| Platinum sensitivity | | | 0.002 |
| sensitive | 52 (60) | 63 (82) | |
| resistance | 35 (40) | 14 (18) | |

In conclusion, SPAG5 is an important novel gene implicated in the survival of BC & OVC cells. Its protein expression is an independent predictor for Anthracycline/cisplatinum CT. SPAG5 may provide new avenues for the discovery of new predictive marker to guide therapeutic intervention.

The invention claimed is:

1. A method for treating a subject having cancer, the method comprising:
   selecting a subject having cancer;
   detecting an elevated expression level of SPAG5 in a tumour tissue sample from said selected subject relative to a SPAG5 reference value; and
   administering, based on said detecting, to the selected subject a platinum chemotherapy agent, an anthracycline, HERCEPTIN® (trastuzumab), or a combination thereof.

2. The method according to claim 1, wherein the selected subject is exhibiting a high expression level of SPAG5 protein or a high level of mRNA relative to a SPAG5 reference value.

3. The method according to claim 1, wherein the SPAG5 reference value is the level of SPAG5 expression in normal tissues or is standard histo-pathological criteria.

4. The method of claim 1, wherein the selected subject is a human.

5. The method of claim 1, wherein the selected subject has a cancer selected from breast cancer, ovarian cancer, gastric cancer, pancreatic cancer, prostate cancer, head and neck cancers, lung cancer or colorectal cancer.

6. A method for treating a subject having cancer, the method comprising:
   selecting a subject having cancer;
   detecting (i) an elevated expression level of SPAG5 in a tumour tissue sample from said subject relative to a SPAG5 reference value and (ii) an H-Score of greater than 10 in the tumour tissue sample from said subject; and
   administering, based on said detecting, to the selected subject a platinum chemotherapy agent, an anthracycline, HERCEPTIN® (trastuzumab), or a combination thereof.

7. The method of claim 6, wherein the selected subject is a human.

8. The method of claim 6, wherein the selected subject has a cancer selected from breast cancer, ovarian cancer, gastric cancer, pancreatic cancer, prostate cancer, head and neck cancers, lung cancer or colorectal cancer.

\* \* \* \* \*